(12) United States Patent
Takahashi et al.

(10) Patent No.: US 11,939,404 B2
(45) Date of Patent: Mar. 26, 2024

(54) METHOD FOR PRODUCING CYCLIZED PEPTIDE HAVING INTRAMOLECULAR S-S BOND

(71) Applicant: AJINOMOTO CO., INC., Tokyo (JP)

(72) Inventors: Daisuke Takahashi, Kawasaki (JP); Tatsuji Inomata, Yokkaichi (JP); Yuki Shinohara, Yokkaichi (JP)

(73) Assignee: AJINOMOTO CO., INC., Tokyo (JP)

( * ) Notice: Subject to any disclaimer, the term of this patent is extended or adjusted under 35 U.S.C. 154(b) by 172 days.

(21) Appl. No.: 17/319,346

(22) Filed: May 13, 2021

(65) Prior Publication Data

US 2021/0277063 A1 Sep. 9, 2021

Related U.S. Application Data

(63) Continuation of application No. PCT/JP2019/044962, filed on Nov. 15, 2019.

(30) Foreign Application Priority Data

Nov. 16, 2018 (JP) ................... 2018-216024

(51) Int. Cl.
C07K 7/64 (2006.01)
C07K 1/06 (2006.01)
C07K 1/107 (2006.01)

(52) U.S. Cl.
CPC .............. *C07K 7/64* (2013.01); *C07K 1/061* (2013.01); *C07K 1/107* (2013.01)

(58) Field of Classification Search
CPC .......... C07K 7/64; C07K 1/061; C07K 1/107; C07K 1/067; C07K 1/1133; Y02P 20/55
See application file for complete search history.

(56) References Cited

U.S. PATENT DOCUMENTS

| 7,304,036 | B2 | 12/2007 | Currie et al. |
| 2014/0018307 | A1 | 1/2014 | Sanghvi et al. |
| 2017/0240599 | A1 | 8/2017 | Vadlamani et al. |
| 2019/0055278 | A1* | 2/2019 | Rao .......................... C07K 1/04 |
| 2020/0002382 | A1 | 1/2020 | Sun et al. |

FOREIGN PATENT DOCUMENTS

| CN | 106167514 A | 11/2016 |
| CN | 106967155 A | 7/2017 |
| JP | 10-310600 | 11/1998 |
| WO | 01/064716 A1 | 9/2001 |
| WO | 2014/188011 A2 | 11/2014 |
| WO | 2017/134687 A1 | 8/2017 |

OTHER PUBLICATIONS

Extended European Search Report dated Aug. 19, 2022 in European Patent Application No. 19884349.2, 9 pages.
Annis. I., et al., "Disulfide bond Formation in Peptides". Biomembranes: Transport Theory: Cells and Model Membranes; [Methods In Enzymology, ISSN 0076-6879], Elsevier, Academic Press, NL. vol. 289, Jan. 1, 1997 (Jan. 1, 1997), pp. 198-221, XP008063663.
Armishaw, C. J., et al., "Conotoxins as Research Tools and Drug Leads", Current Protein and Peptide Science, Bentham Science Pulbishers, NL, vol. 6, No. 3, Jun. 1, 2005 (Jun. 1, 2005), pp. 221-240. XP00907S753.
Internatioanl Search Report dated Feb. 4, 2020 in International Application No. PCT/JP2019/044962.
Combined Chinese Office Action and Search Report dated Aug. 12, 2023 in Chinese Application 201980074871.9, (with partial unedited computer-generated English translation), 10 pages.
Wang, De-Xin, "Progress in Synthesis of Cyclopeptides", Chinese Journal of Organic Chemistry vol. 28, No. 4, pp. 549-573 (with English abstract).
Wang, Liang-You et al., "Methods of Disulfide Formation in Peptide Synthesis", Chinese Journal of Organic Chemistry, vol. 18, No. 6, 1998, pp. 576-580 (with English abstract on p. 580).

* cited by examiner

*Primary Examiner* — Sudhakar Katakam
(74) *Attorney, Agent, or Firm* — Oblon, McClelland, Maier & Neustadt, L.L.P.

(57) ABSTRACT

Cyclized peptides having a crosslinked structure by one or more intramolecular S—S bonds may be prepared by:
(1-A) as to a completely protected linear peptide having two or more SH groups as functional groups on the peptide, removing protecting groups of all functional groups other than the protected SH groups in the peptide,
(1-B) protecting all SH groups of the linear peptide having two or more SH groups as the functional groups on the peptide by forming a temporary S—S bond, and
(2) subjecting the peptide obtained by step (1-A) and step (1-B) to a folding step under oxidation and reduction conditions to obtain the cyclized peptide by re-forming an S—S bond in the peptide molecule.

31 Claims, 1 Drawing Sheet
Specification includes a Sequence Listing.

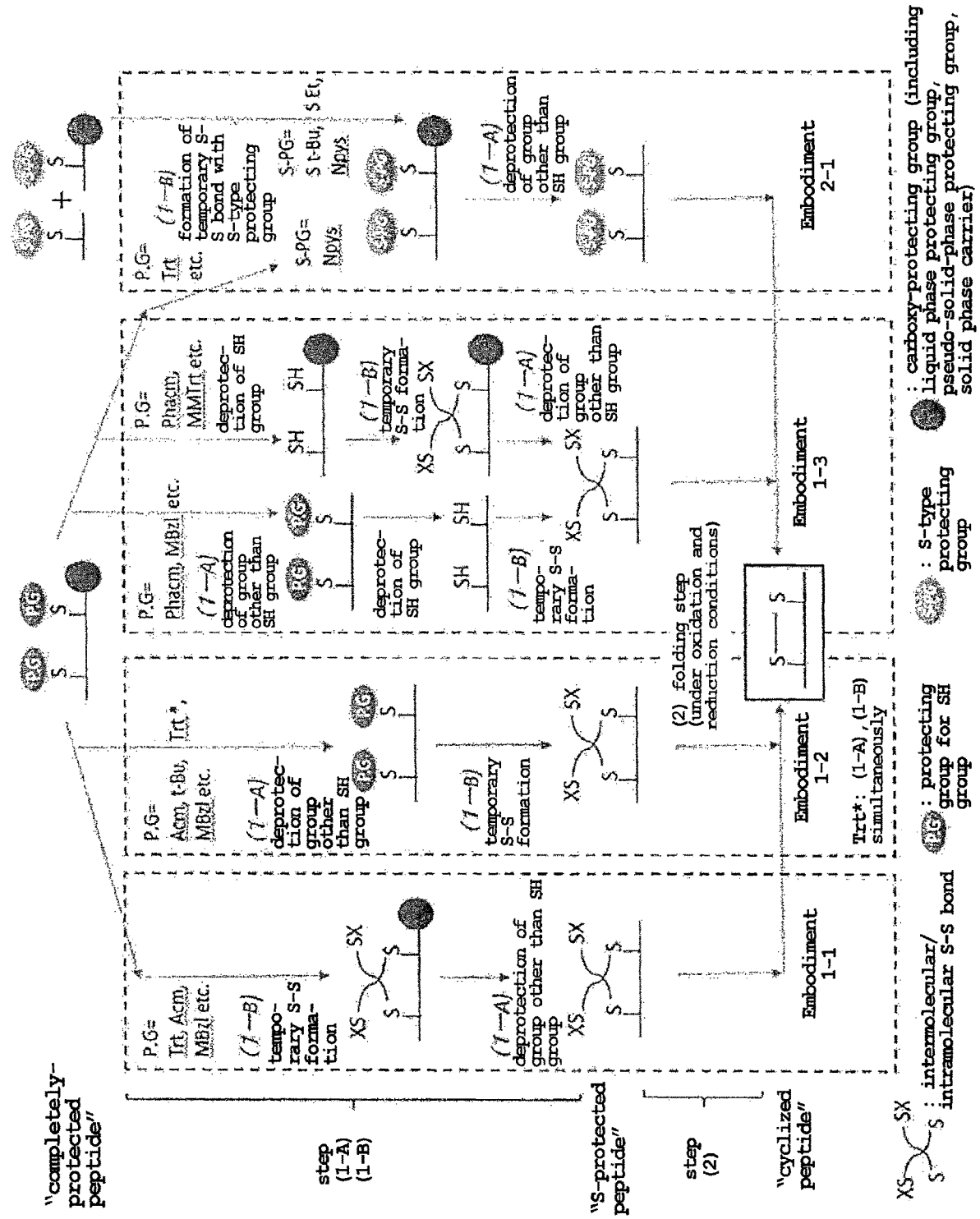

METHOD FOR PRODUCING CYCLIZED PEPTIDE HAVING INTRAMOLECULAR S-S BOND

CROSS REFERENCES TO RELATED APPLICATIONS

This application is a continuation of International Patent Application No. PCT/JP2019/044962, filed on Nov. 15, 2019, and claims priority to Japanese Patent Application No. 2018-216024, filed on Nov. 16, 2018, both of which are incorporated herein by reference in their entireties.

BACKGROUND OF THE INVENTION

Field of the Invention

The present invention relates to methods for producing a cyclized peptide having a crosslinked structure due to an intramolecular S—S bond (disulfide bond), and is useful in the field of peptide synthesis.

DISCUSSION OF THE BACKGROUND

Many peptides containing S—S bond have long been known as peptide pharmaceutical products, such as somatostatin, octreotide, atosiban and the like. In recent years, research and development of cyclized peptides containing four or more SH groups in the molecule and having cyclization sites due to a plurality of S—S cross-linked structures from S—S bonds intramolecularly formed by the SH groups (for example, linaclotide, plecanatide, ziconotide, insulin detemir, insulin glulisine, etc.) are underway.

Conventionally, in the synthesis of a peptide cyclized by the formation of an intramolecular S—S bond, a linear peptide corresponding to the amino acid sequence of the cyclized peptide of interest is produced, all the protective groups of the functional groups of the constituent amino acid residues, including the SH group-protecting group, are removed to obtain an unprotected linear peptide, and a cyclized peptide having a desired crosslinked structure is synthesized by forming an S—S bond with the thus-obtained peptide under oxidative conditions (e.g., WO 2014/188011, which is incorporated herein by reference in its entirety). In WO 2014/188011, acids such as trifluoroacetic acid (TFA) and the like are used to remove all protecting groups that the peptide has, which in turn deprotects the SH group in the peptide. As a result, problems occur in that the debris of the protecting groups and the like cause alkylation of the SH group, decrease the yield, and the impurities thereof decrease the yield of the peptide of interest in the successive cyclization reaction.

Regarding the decrease in the yield of the desired peptide in the cyclization reaction due to the by-produced impurities, WO 2017/134687, which is incorporated herein by reference in its entirety, describes a production method of peptide, including removing the protecting group of the functional group of amino acid residues other than the cysteine residue of linear peptide while protecting the SH group by using a phenylacetamidomethyl group (Phacm group) as the protecting group of the SH group of the cysteine residue, followed by removal of the Phacm protecting group and formation of S—S bond under solid phase conditions.

In the production of a cyclized peptide containing 4 or more SH groups, since there are two or more combinations of S—S bond formation, it is necessary to selectively form an S—S bond between SH groups of interest in the production step. Regarding the decreased yield of the cyclization reaction, the impurity in which the SH group is alkylated in the peptide may have an odd number of SH groups in the molecule, in which case problems occur since desired plural S—S bonds cannot be formed, unprotected SH group remains in the peptide, resulting in intermolecular side reaction products, and the SH group itself acts as a reducing agent to cause a side reaction that cleaves the S—S bond formed and reduces the cyclization yield.

In this connection, U.S. Pat. No. 7,304,036, which is incorporated herein by reference in its entirety, describes a production method of peptide under solid phase conditions, including designing a linear peptide in which the SH group is protected in advance with a different type of protecting group (acetamidomethyl group (Acm group) and 4-methylbenzyl group) according to the combination of SH groups in the peptide for which formation of an S—S bond is intended, and sequentially repeating a deprotection step of the SH group-protecting group and an oxidation step according to the type of the protecting group so as to form an S—S bond between the desired SH groups in the peptide.

In addition to the above, in the conventional methods, the cyclization reaction by intramolecular S—S bond formation generally needs to be performed under low concentration conditions (under excessive use of solvent) to suppress the progress of the side reaction of S—S bond formation between molecules. The extremely low production efficiency also poses problems. Therefore, there has been a demand for a highly efficient production method capable of effectively performing the desired cyclization reaction even when the substrate concentration during the cyclization reaction is increased.

SUMMARY OF THE INVENTION

In the pertinent technical field, studies have conventionally been made to solve the problems in producing a cyclized peptide having an S—S crosslinked structure. However, all of them are based on the formation of S—S bond by the selection of a protecting group for the SH group in the peptide. Therefore, the development of a new convenient and efficient production method of cyclized peptide has been demanded. The present invention resolves such problems.

This and other objects, which will become apparent during the following detailed description, have been achieved by the inventors' discovery of methods for producing a cyclized peptide that commonly include a step of efficiently obtaining a cyclized peptide of interest based on a new methodology in which, a peptide having two or more SH groups as functional groups on the peptide, wherein an S—S bond is temporarily formed with all SH groups intermolecularly or intramolecularly by various preparation methods, and other functional groups on the peptide are unprotected, is subjected to a folding step under oxidation and reduction conditions to form an S—S bond again in the molecule of the peptide, and completed the present invention. Specifically, the present invention provides a production method of a cyclized peptide including the following steps.

(1) A method for producing a cyclized peptide, comprising (1-A) as to a linear peptide having two or more SH groups as functional groups on the peptide, in which all SH groups are protected, an N terminal amino group is optionally protected, and all of a C-terminal carboxy group and other functional groups on the peptide are protected (hereinafter sometimes to be referred to as "completely-protected peptide" in the present specification), a step of removing protecting groups of all functional groups other than the protected SH groups in the peptide, (1-B) a step of protecting all SH groups of the linear peptide having two or more SH groups as the functional groups on the peptide by forming a temporary S—S bond, and (2) a step of subjecting the peptide obtained by the above-mentioned step (1-A) and step (1-B), in which two or more SH groups are present as the functional groups on the peptide, all SH groups are protected by formation of a temporary S—S bond, and all protecting groups of other functional groups on the peptide are removed (hereinafter sometimes to be referred to as "S-protected peptide" in the present specification) to a folding step under oxidation and reduction conditions to obtain the cyclized peptide by re-forming an S—S bond in the peptide molecule.

In step (1-A), the protection of the SH group in the completely-protected peptide includes both embodiments of protecting with the below-mentioned protecting group of SH group, and protecting by the formation of a temporary S—S bond.

In the present invention, the S-protected peptide of step (2) can be obtained by performing step (1-A) and step (1-B). The order of step (1-A) and step (1-B) is not limited to this order and can be appropriately changed according to the embodiments. Therefore, step (1-B) may be performed after step (1-A), step (1-A) may be performed after step (1-B), these may be combined, or the both steps may be performed simultaneously, all of these cases are encompassed in the scope of the present invention (hereinafter step (1-A) and step (1-B) are sometimes to be collectively referred to as step (1)).

(2) The production method of a cyclized peptide of (1), wherein the protection of all SH groups by forming a temporary S—S bond in step (1-B) is performed by "forming a temporary S—S bond with all SH groups within peptide molecules and/or between peptide molecules" (hereinafter sometimes to be referred to as "temporary S—S formation" in the present specification), or the protection of all SH groups by forming a temporary S—S bond in step (1-B) is performed by forming a temporary S—S bond with an S-type protecting group.

(3) The production method of a cyclized peptide of (1) or (2), wherein the S-protected peptide is obtained by any one of the following steps:

(1) a step of obtaining the S-protected peptide by subjecting the completely-protected peptide to temporary S—S formation in step (1-B) to obtain a mixture of peptides crosslinked or linked by a temporary S—S bond (hereinafter sometimes to be referred to as "temporary S—S formed peptide mixture" in the present specification), and removing the protecting groups of all functional groups other than the SH group protected by temporary S—S bond formation in the temporary S—S formed peptide mixture in step (1-A);

(2) a step of obtaining the S-protected peptide by removing the protecting groups of all functional groups other than the SH group of the completely-protected peptide in step (1-A), and then or simultaneously subjecting the deprotected peptide to temporary S—S formation in step (1-B) to obtain a temporary S—S formed peptide mixture;

(3) a step of obtaining the S-protected peptide by a)
1) after removing the protecting groups of all functional groups other than the SH group in step (1-A), 2) removing the protecting group of the SH group, and further 3) carrying out temporary S—S formation in step (1-B) to obtain a temporary S—S formed peptide mixture, or b)
1) after removing the protecting group of the SH group of the completely-protected peptide, 2) carrying out temporary S—S formation in step (1-B) to obtain a temporary S—S formed peptide mixture, and further 3) removing the protecting groups of all functional groups other than the SH group protected by temporary S—S bond formation in the temporary S—S formed peptide mixture in step (1-A); and (4) a step of obtaining the S-protected peptide by re-protecting protecting groups of SH groups of a linear peptide having two or more SH groups as functional groups on the peptide, in which an N terminal amino group is optionally protected, and all of a C-terminal carboxy group and other functional groups on the peptide are protected, with an S-type protecting group, or protecting same with an S-type protecting group in advance to obtain a peptide in which all SH groups are protected by formation of a temporary S—S bond with the S-type protecting group in step (1-B), and removing the protecting groups of all functional groups other than the SH group protected by the temporary S—S bond in the peptide in step (1-A).

(4) The production method of a cyclized peptide of any of (1) to (3), wherein the protection of all SH groups by forming a temporary S—S bond in step (1-B) is performed by temporary S—S formation.

(5) The production method of a cyclized peptide of (4), wherein the temporary S—S formation is performed by an iodine treatment or a thallium (III) trifluoroacetate treatment.

(6) The production method of a cyclized peptide of (5), wherein the temporary S—S formation is performed by the iodine treatment.

(7) The production method of a cyclized peptide of any of (1) to (6), wherein the S-protected peptide is obtained by subjecting the completely-protected peptide to the temporary S—S formation to obtain the temporary S—S formed peptide mixture in step (1-B), and removing the protecting groups of all functional groups other than the SH group protected by temporary S—S bond formation in the temporary S—S formed peptide mixture in step (1-A).

(8) The production method of a cyclized peptide of (7), wherein the protecting group of the SH group in the completely-protected peptide is a protecting group other than an S-type protecting group.

(9) The production method of a cyclized peptide of (8), wherein the protecting group of the SH group in the completely-protected peptide is a trityl group (Trt group), an acetamidomethyl group (Acm group), a benzyl group (Bzl group), a 4-methylbenzyl group (4-MeBzl group), or a 4-methoxybenzyl group (MBzl group).

(10) The production method of a cyclized peptide of any of (7) to (9), wherein the temporary S—S formation is performed by an iodine treatment or a thallium (III) trifluoroacetate treatment.

(11) The production method of a cyclized peptide of (10), wherein the temporary S—S formation is performed by an iodine treatment.

(12) The production method of a cyclized peptide of any of (1) to (4), wherein the S-protected peptide is obtained by removing the protecting groups of all functional groups other than the SH group of the completely-protected peptide in step (1-A), and then or simultaneously subjecting the deprotected peptide to temporary S—S formation in step (1-B) to obtain a temporary S—S formed peptide mixture.

(13) The production method of a cyclized peptide of (12), wherein the protecting group of the SH group of the completely-protected peptide is a protecting group other than an S-type protecting group.

(14) The production method of a cyclized peptide of (13), wherein the protecting group of the SH group of the completely-protected peptide is an acetamidomethyl group (Acm group), a t-butyl group (t-Bu group), a trityl group (Trt group), a benzyl group (Bzl group), a 4-methylbenzyl group (4-MeBzl group), or a 4-methoxybenzyl group (MBzl group).

(15) The production method of a cyclized peptide of any of (12) to (14), wherein the temporary S—S formation is performed by an iodine treatment, a DMSO/TFA treatment, or a thallium (III) trifluoroacetate treatment.

(16) The production method of a cyclized peptide of (15), wherein the temporary S—S formation is performed by an iodine treatment.

(17) The production method of a cyclized peptide of any of (1) to (4), wherein the S-protected peptide is obtained by a)
 1) after removing the protecting groups of all functional groups other than the SH group in step (1-A),
 2) removing the protecting group of the SH group, and further
 3) carrying out temporary S—S formation in step (1-B) to obtain a temporary S—S formed peptide mixture, or b)
 1) after removing the protecting group of the SH group of the completely-protected peptide,
 2) carrying out temporary S—S formation in step (1-B) to obtain a temporary S—S formed peptide mixture, and further
 3) removing the protecting groups of all functional groups other than the SH group protected by temporary S—S bond formation in the temporary S—S formed peptide mixture in step (1-A).

(18) The production method of a cyclized peptide of (17), wherein the protecting group of the SH group is a protecting group other than an S-type protecting group.

(19) The production method of a cyclized peptide of (18), wherein the protecting group of the SH group is a phenylacetamidomethyl group (Phacm group), a 4-methoxybenzyl group (MBzl group), or a mono methoxytrityl group (MMTrt group).

(20) The production method of a cyclized peptide of (19), wherein the protecting group of the SH group is removed by a treatment with an aqueous solution in the presence of penicillin amidohydrolase (PGA), a treatment with DDQ, or a treatment with a weak acid.

(21) The production method of a cyclized peptide of any of (17) to (20), wherein the temporary S—S formation is performed by an iodine treatment, an Npys-OMe treatment, or a thallium (III) trifluoroacetate treatment.

(22) The production method of a cyclized peptide of (21), wherein the temporary S—S formation is performed by an iodine treatment.

(23) The production method of a cyclized peptide of any of (1) to (3), wherein the protection of all SH groups by forming a temporary S—S bond in step (1-B) is performed by forming a temporary S—S bond with an S-type protecting group.

(24) The production method of a cyclized peptide of (23), wherein the protection of all SH groups by forming a temporary S—S bond in step (1-B) is performed by re-protecting the SH group with an S-type protecting group instead of a protecting group other than an S-type protecting group.

(25) The production method of a cyclized peptide of (23) or (24), wherein the S-type protecting group is a 3-nitro-2-pyridinesulfenyl group (Npys group), a t-butylmercapto group (S-tBu group), or an ethylmercapto group (S-Et group).

(26) The production method of a cyclized peptide of any of (1) to (3) or (23) to (25), wherein the S-protected peptide is obtained by re-protecting protecting groups of SH groups of a linear peptide having two or more SH groups as functional groups on the peptide, in which an N terminal amino group is optionally protected, and all of a C-terminal carboxy group and other functional groups on the peptide are protected, with an S-type protecting group, or protecting same with an S-type protecting group in advance to obtain a peptide in which all SH groups are protected by formation of a temporary S—S bond with the S-type protecting group in step (1-B), and removing the protecting groups of all functional groups other than the SH group protected by the temporary S—S bond in the peptide in step (1-A).

(27) The production method of a cyclized peptide of any of (1) to (26), wherein the deprotection is performed in the absence of a reducing agent.

(28) The production method of a cyclized peptide of any of (1) to (27), wherein the folding step under the oxidation and reduction conditions in step (2) is performed in an aqueous solution with pH 6 or higher.

(29) The production method of a cyclized peptide of any of (1) to (28), wherein the folding step under the oxidation and reduction conditions in step (2) is performed in the co-presence of an oxidant and a reducing agent.

(30) The production method of a cyclized peptide of any of (1) to (29), wherein the number of SH groups as the functional group on the peptide of the S-protected peptide is 2.

(31) The production method of a cyclized peptide of any of (1) to (29), wherein the number of SH groups as the functional group on the peptide of the S-protected peptide is not less than 4.

(32) The production method of a cyclized peptide of any of (1) to (31), wherein the number of SH groups as the functional group on the peptide of the S-protected peptide is an even number.

Advantageous Effects of Invention

In the present invention, a cyclized peptide can be obtained efficiently in a folding step in which SH groups are protected by forming a temporary S—S bond, while overcoming the problems of conventional methods such as a decrease in the yield by alkylation of SH groups due to the debris of deprotected various kinds of protecting groups and the like, and a decrease in the yield of the desired cyclization reaction due to the by-produced impurities. In the present invention, a cyclization reaction can be effectively performed even under comparatively high concentration conditions. Thus, the present invention is also highly superior from the aspect of production efficiency.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the outline of the embodiments of the present invention. In the FIGURE, the "embodiment 1-1", "embodiment 1-2", "embodiment 1-3" and "embodiment 2-1" correspond to the embodiments in step (1-A) and step (1-B).

DETAILED DESCRIPTION OF THE PREFERRED EMBODIMENTS

As described above, the embodiment to be the basis of the present invention is a production method of a cyclized peptide having a crosslinked structure by an intramolecular S—S bond, including the following steps.
(1) A method for producing a cyclized peptide, comprising
(1-A) as to a linear peptide having two or more SH groups as functional groups on the peptide, in which all SH groups are protected, an N terminal amino group is optionally protected, and all of a C-terminal carboxy group and other functional groups on the peptide are protected ("completely-protected peptide"), a step of removing protecting groups of all functional groups other than the protected SH groups of the peptide,
(1-B) a step of protecting all SH groups of the linear peptide having two or more SH groups as the functional groups on the peptide by forming a temporary S—S bond,
and
(2) a step of subjecting the peptide obtained by the above-mentioned step (1-A) and step (1-B), in which two or more SH groups are present as the functional groups on the peptide, all SH groups are protected by formation of a temporary S—S bond, and all protecting groups of other functional groups on the peptide are removed ("S-protected peptide") to a folding step under oxidation and reduction conditions to obtain the cyclized peptide by re-forming an S—S bond in the peptide molecule.

The present invention is described in detail below. Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferred methods and materials are described in the following. All publications and patents referred to in the present specification are hereby incorporated by reference so as to describe and disclose constructed products and methodology described in, for example, publications usable in relation to the described invention.

Step (1-A), and Step (1-B)

The "completely-protected peptide" used in this step can be produced by those skilled in the art by producing a structural unit such as an amino acid or the like in which a terminal amino group, a terminal carboxy group, and functional groups including SH group are appropriately protected by protecting groups known in the art, according to the sequence of the desired cyclized peptide, by using known starting materials, or purchasing the structural unit, and repeating a deprotection reaction and a peptide chain elongation reaction according to a method known per se or a method similar thereto. The SH group can also be protected by forming a temporary S—S bond after peptide synthesis, which is described later.

The cyclized peptide of interest may be either naturally occurring or non-naturally occurring.

An amino acid etc. which is a constitutional unit of a peptide produced by the method of the present invention is a compound having an amino group and a carboxy group in the same molecule, and may be a natural amino acid or non-natural amino acid, and an L form, a D form or a racemate. The constitutional unit is not limited to amino acids, and may be other compounds applicable to peptide synthesis (hereinafter referred to as amino acid analogs). Those of ordinary skill in the art can appropriately select such amino acid analogs and produce them according to a method known per se or a method similar thereto, or purchase them.

Examples of the SH group as a functional group on the peptide include, but are not limited to, the SH groups contained in a cysteine residue, a homocysteine residue, a 3-mercaptopropionyl group, and the like.

The position of the SH group as a functional group on the peptide is not particularly limited for any residue as long as it is present in the peptide sequence. It may be located at the terminal or the middle of the peptide sequence, or may be adjacent to each other. Also, SH groups may be present in a plurality of chains, such as insulin produced by cutting out from proinsulin.

A protecting group for an N-terminal amino group, a protecting group for a C-terminal carboxy group, and a protecting group for a functional group on a peptide of a constitutional unit other than an amino acid having an SH group as a functional group on a peptide, or an amino acid analog can be selected from those generally used in the pertinent technical field. A suitable protecting group for achieving the purpose of step (1-A) can be selected according to the selection of the protecting group for the SH group in step (1-A).

This step (1-A) refers to a process for removing the protecting groups (including the pseudo-solid-phase protecting group and solid phase carrier described later) of all functional groups other than the protected SH group possessed by the "completely-protected peptide".

The deprotection in this step (1-A) also includes cutting out pseudo-solid-phase protecting groups and solid phase carriers. The deprotection in this step (1-A) can be performed by methods generally used in the pertinent technical field, according to the protecting groups used. Since it is necessary to prevent removal of the protecting group of the SH group at the time of deprotection here, the deprotecting method is desirably selected as appropriate according to the protecting group of the SH group. Particularly, when the SH group is protected by the below-mentioned temporary S—S bond, it is appropriate to select one that can be removed in the absence of a reducing agent. A more specific deprotection method is described later.

This step (1-B) refers to a process for protecting all SH groups by formation of a temporary S—S bond in a linear peptide having two or more SH groups as the functional groups on the peptide.

The formation of a temporary S—S bond is performed by the formation of a temporary S—S bond with an S-type protecting group or the formation of a temporary S—S bond by temporary S—S formation. The details thereof, including protecting groups for the SH groups, are described later according to the embodiment.

The formation of a temporary S—S bond in step (1-B) is performed at an appropriate timing such as before or after removal of the protecting groups of all functional groups other than the SH group (also including pseudo-solid-phase protecting group described later) (step (1-A)), or simultaneously therewith. The relationship of before and after between step (1-A) and step (1-B) is determined as appropriate in relation to the protecting group of the SH group used, the reaction mode of temporary S—S bond formation, the deprotection conditions of the protecting group other than the SH group, and the like. Preferred specific embodiments are described later.

Step (1-A) and step (1-B) can be performed under solid phase conditions or liquid phase conditions (including pseudo-solid-phase conditions using pseudo-solid-phase protecting group). Those of ordinary skill in the art can appropriately select the conditions of solid phase and liquid phase (pseudo-solid-phase using pseudo-solid-phase protecting group) according to the synthesis strategies such as the structure of the cyclized peptide of interest, purpose of production (production scale, etc.) and the like.

When step (1-A) and step (1-B) are performed under solid phase conditions, at least one of the functional groups on the peptide, such as the terminal carboxy group, the functional group on the peptide (e.g., carboxy group) and the like is supported on a solid phase carrier by a conventional method in peptide synthesis under solid phase conditions.

The solid phase carrier may be any solid phase carrier known in the pertinent technical field and suitable for use in solid phase synthesis. In the present specification, the term "solid phase" includes that a peptide is bonded or linked to the above-mentioned solid phase carrier via a conventionally-used functional linker or handle group. A "solid phase" in this context also includes such linker. Examples of the solid phase include polystyrene supports (which may be further functionalized by, for example, p-methylbenzylhydrylamine), rigid functionized supports such as diatomaceous earth-encapsulated polydimethylacrylamide (pepsin K), silica, microporous glass, and the like. The solid phase resin matrix may be composed of an amphiphilic polystyrene-PEG resin or PEG-polyamide or PEG-polyester resin. The solid phase carrier also includes, for example, Wang-PEG resin (Alko-PEG Resin), SAL-PEG Resin, and Rink-amide PEG resin.

Various protecting groups used for the peptide of the present invention are described in the following. Each protecting group can be introduced into each functional group according to a method generally practiced in the pertinent technical field.

When the SH group in the "completely-protected peptide" is protected by a protecting group, examples of the protecting group include the protecting group other than the S-type protecting group (e.g., t-butyl group (t-Bu group), triphenyl methyl group (trityl group: Trt group), methyltrityl group, methoxytrityl group, mono methoxytrityl group (MMTrt group), adamantyl group (Ad group), acetamidomethyl group (Acm group), trimethylacetamidomethyl group, phenylacetamidomethyl group (Phacm group), benzyl group (Bzl group), 4-methylbenzyl group (4-MeBzl group), 3-methylbenzyl group, 2-methylbenzyl group, 4-methoxybenzyl group (MBzl group), 3-methoxybenzyl group, 2-methoxybenzyl group, 2,4,6-trimethoxy benzyl group, dabsyl group (Dbs group: 4-dimethylaminoazo benzene-4'-sulfonyl group) etc.), and S-type protecting group (e.g., 3-nitro-2-pyridinesulfenyl group (Npys group), t-butylmercapto group (S-tBu group), ethylmercapto group (S-Et group) etc.). These are not limitative, and those of ordinary skill in the art can appropriately select the protecting group of SH group according to the overall synthesis strategies for enforcing the present invention. Preferred embodiments are described later.

The protecting group of the functional group other than the SH group possessed by the "completely-protected peptide" is explained below.

Protecting Group of N Terminal Amino Group

While not always necessary when performing step (1-A), as the protecting group (temporary protecting group) for the N-terminal amino group, for example, a 9-fluorenylmethyloxycarbonyl group (hereinafter to be also referred to as Fmoc group), a tert-butoxycarbonyl group (hereinafter to be also referred to as Boc group), and the like can be mentioned. Preferred is an Fmoc group.

Protecting Group of C-Terminal Carboxy Group

Examples of the protecting group of C-terminal carboxy group include an ester-type protecting group, an amide-type protecting group, a hydrazide-type protecting group and the like.

As the ester-type protecting group, substituted or unsubstituted alkyl ester, and substituted or unsubstituted aralkyl ester are preferably used. As the substituted or unsubstituted alkyl ester, methyl ester, ethyl ester, tert-butyl ester, cyclohexyl ester, trichloroethyl ester, phenacyl ester and the like are preferably used. As the substituted or unsubstituted aralkyl ester, benzyl ester, p-nitrobenzyl ester, p-methoxybenzyl ester, diphenylmethyl ester, 9-fluorenylmethyl (Fm) ester, 4-picolyl (Pic) ester and the like are preferably used.

As the amide-type protecting group, unsubstituted amide, primary amide such as N-methylamide, N-ethylamide, N-benzylamide and the like, secondary amide such as N,N-dimethylamide, pyrrolidinylamide, piperidinylamide and the like, and the like are preferably used.

As the hydrazide-type protecting group, unsubstituted hydrazide, N-phenylhydrazide, N,N'-diisopropylhydrazide and the like are preferably used.

Protecting Group for Functional Group on Peptide

Examples of the protecting group for the functional group on peptide include the protecting groups described in PEPTIDE GOUSEI NO KISO TO JIKKEN, published by Maruzen Co., Ltd. (1985), PROTECTIVE GROUPS IN ORGANIC SYNTHESIS, the third edition, published by JOHN WILLY&SONS (1999), which are incorporated herein by reference in their entireties, and the like.

When the functional group on peptide is an amino group, a urethane-type protecting group, an acyl-type protecting group, a sulfonyl-type protecting group and the like can be mentioned.

As the urethane-type protecting group, for example, a methoxycarbonyl group, an ethoxycarbonyl group, a tert-butoxycarbonyl (Boc) group, and the like are used. Of these, a Boc group is particularly preferably used since selective deprotection thereof is possible under mild acidic conditions.

As the acyl-type protecting group, for example, a formyl group, an acetyl group, a trifluoroacetyl group and the like are preferably used.

As the sulfonyl-type protecting group, for example, a p-toluenesulfonyl (Ts) group, a p-tolylmethanesulfonyl group, a 4-methoxy-2,3,6-trimethylbenzenesulfonyl group and the like are preferably used.

When the functional group on peptide is a carboxy group, the same protecting groups as those recited above as the protecting group of the C-terminal carboxy group can be mentioned.

When the functional group on peptide is a hydroxy group (including phenolic hydroxy group), an alkyl-type protecting group, an alkoxyalkyl-type protecting group, an acyl-type protecting group, an alkylsilyl-type protecting group and the like can be mentioned.

Examples of the alkyl-type protecting group include a methyl group, an ethyl group, a tert-butyl group and the like.

Examples of the alkoxyalkyl-type protecting group include a methoxymethyl group (MOM group), a 2-tetrahydropyranyl group (THP group), an ethoxyethyl group (EE group), and the like.

Examples of the acyl-type protecting group include an acetyl group, a pivaloyl group, a benzoyl group, and the like.

Examples of the alkylsilyl-type protecting group include a trimethylsilyl group (TMS group), a triethylsilyl group (TES group), a tert-butyldimethylsilyl group (TBS group or TBDMS group), a triisopropyl silyl group (TIPS group), a tert-butyldiphenylsilyl group (TBDPS group), and the like.

Other functional groups can also be protected by protecting groups conventionally used in the pertinent technical field. For example, the guanidino group of arginine can be protected by a p-toluenesulfonyl group. The imidazole group of histidine can be protected by a trityl group, a benzyloxymethyl group, and the like. In addition, the indole group of tryptophan can be protected by a formyl group.

While the protecting group for the functional group on peptide is described above, those of ordinary skill in the art can perform this step by appropriately selecting the protecting group according to the protection scheme (e.g., Fmoc/tBu strategy, tBu/Bzl strategy, Bzl/tBu strategy, etc.) selected in the technical field according to the overall synthetic strategy for carrying out the present invention. Among these, the Fmoc/tBu strategy is preferred.

When the present invention is performed under liquid phase conditions, the C-terminal carboxy group is desirably protected, and when the functional group on peptide is a carboxy group, at least one of the carboxy groups is desirably protected. As the protecting group of the carboxy group, the protecting groups (ester type protecting group, amide type protecting group, hydrazide type protecting group, etc.) recited as the aforementioned "protecting group of C-terminal carboxy group" can be mentioned. Among these, ester type protecting group is preferred. As the ester-type protecting group, substituted or unsubstituted alkyl ester, and substituted or unsubstituted aralkyl ester are preferably used. As the substituted or unsubstituted alkyl ester, methyl ester, ethyl ester, tert-butyl ester, cyclohexyl ester, trichloroethyl ester, phenacyl ester and the like are preferably used. As the substituted or unsubstituted aralkyl ester, benzyl ester, p-nitrobenzyl ester, p-methoxybenzyl ester, diphenylmethyl ester, 9-fluorenylmethyl (Fm) ester, 4-picolyl (Pic) ester and the like are preferably used. Particularly, tert-butylester, benzylester and the like are preferred.

Pseudo-Solid-Phase Protecting Group

When the present invention is performed under liquid phase conditions, the C-terminal carboxy group and, when the functional group on peptide is a carboxy group, at least one of the carboxy groups may be protected where necessary by a pseudo-solid-phase protecting group (hereinafter sometimes to be referred to as "anchor" in the present specification) to facilitate purification. While the purification method of a peptide using a pseudo-solid-phase protecting group is not particularly limited, a method known per se (JP-A-2000-44493, WO 2006/104166, WO 2007/034812, WO 2007/122847, WO 2010/113939, WO 2010/104169, WO 2011/078295, WO 2012/029794, all of which are incorporated herein by reference in their entireties, and the like) or a method according thereto can be performed. The pseudo-solid-phase protecting group here refers to a group containing an anchor soluble in halogenated solvents or ether solvents, insoluble in polar solvents and having a molecular weight of not less than 300 (e.g., benzyl compound, diphenylmethane compound or fluorene compound), and capable of condensing with a carboxy group.

One embodiment of the above-mentioned anchor soluble in halogenated solvents or ether solvents, insoluble in polar solvents and having a molecular weight of not less than 300 is a compound represented by the following formula (I). Among such compounds, one having a molecular weight of not less than 400 is preferred. The formula (I):

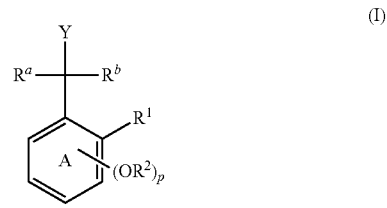

wherein $R^1$ is a hydrogen atom or, when $R^b$ is a group represented by the following formula (a), optionally shows a single bond together with $R^3$ to form a fluorene ring together with ring A and ring B;

$R^2$ in the number of p is each independently an organic group having an aliphatic hydrocarbon group;

p is an integer of 1 to 4;

ring A optionally further has, in addition to $OR^2$ in the number of p, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom, or a phenyl group optionally substituted by a halogen atom; and $R^b$ is a hydrogen atom, or a group represented by the formula (a):

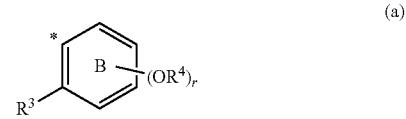

wherein * is a binding site;

r is an integer of 0 to 4;

$R^4$ in the number of r is each independently an organic group having an aliphatic hydrocarbon group;

$R^3$ is a hydrogen atom, or optionally shows a single bond together with $R^1$ to form a fluorene ring together with ring A and ring B; and ring B optionally further has, in addition to $OR^4$ in the number of r, a substituent selected from the group consisting of a halogen atom, a $C_{1-6}$ alkyl group optionally substituted by a halogen atom, and a $C_{1-6}$ alkoxy group optionally substituted by a halogen atom; and Y is a hydroxy group, NHR (R is a hydrogen atom, an alkyl group or an aralkyl group) or a halogen atom.

The anchor represented by the above-mentioned formula (I) is bound to a compound intended to be protected. That is, an anchor wherein Y is a hydroxy group, an —NHR group or a halogen atom protects a compound by condensing with a carboxy group on the C-terminal of amino acid or peptide and the like.

In the present specification, as the "alkyl group" for R, a straight or branched $C_{1-30}$ alkyl group can be mentioned. It is preferably a $C_{1-10}$ alkyl group, more preferably a $C_{1-6}$ alkyl group. Specific preferred examples include methyl, ethyl, propyl, isopropyl, butyl, isobutyl, sec-butyl, tert-butyl and the like, and methyl and ethyl are particularly preferred.

In the present specification, as the "aralkyl group" for R, a $C_{7-30}$ aralkyl group can be mentioned. It is preferably a $C_{7-20}$ aralkyl group, more preferably a $C_{7-6}$ aralkyl group ($C_{6-10}$ aryl-$C_{1-6}$ alkyl group). Specific preferred examples include benzyl, 1-phenylethyl, 2-phenylethyl, 1-phenylpropyl, naphthylmethyl, 1-naphthylethyl, 1-naphthylpropyl and the like, and benzyl is particularly preferred.

As R, a hydrogen atom, a $C_{1-6}$ alkyl group or a $C_{7-16}$ aralkyl group is preferred, a hydrogen atom, methyl, ethyl or benzyl is preferred, and a hydrogen atom is particularly preferred.

In the present specification, the "halogen atom" is a fluorine atom, a chlorine atom, a bromine atom or an iodine atom. In the present specification, as the "halogen atom" for Y, a chlorine atom, a bromine atom or an iodine atom is preferred, and a bromine atom is preferred.

In the present specification, the "organic group having an aliphatic hydrocarbon group" for $R^2$ or $R^4$ is a monovalent organic group having an aliphatic hydrocarbon group in a molecule structure thereof.

The "aliphatic hydrocarbon group" in the "organic group having an aliphatic hydrocarbon group" is a straight or branched saturated or unsaturated aliphatic hydrocarbon group, preferably an aliphatic hydrocarbon group having 5 or more carbon atoms, more preferably an aliphatic hydrocarbon group having 5 to 60 carbon atoms, further preferably an aliphatic hydrocarbon group having 5 to 30 carbon atoms, particularly preferably an aliphatic hydrocarbon group 10 to 30 carbon atoms.

The moiety of the "aliphatic hydrocarbon group" in the "organic group having an aliphatic hydrocarbon group" is not particularly limited, and may be present at the terminal (monovalent group), or other site (e.g., divalent group).

Examples of the "aliphatic hydrocarbon group" include monovalent groups such as an alkyl group, a cycloalkyl group, an alkenyl group, a cycloalkenyl group, an alkynyl group and the like, and divalent groups derived therefrom, preferably monovalent groups such as a methyl group, an ethyl group, a propyl group, an isopropyl group, a butyl group, an isobutyl group, a sec-butyl group, a tert-butyl group, a pentyl group, a hexyl group, an octyl group, a decyl group, a dodecyl group, a lauryl group, a tridecyl group, a myristyl group, a cetyl group, a stearyl group, an arachyl group, a behenyl group, an oleyl group, an isostearyl group and the like, and divalent groups derived therefrom.

The moiety other than the "aliphatic hydrocarbon group" of the "organic group having an aliphatic hydrocarbon group" can be set freely. For example, it may have a moiety such as —O—, —S—, —COO—, —OCONH—, —CONH—, a hydrocarbon group (monovalent group or divalent group) and the like as a linker. Examples of the "hydrocarbon group" include an aliphatic hydrocarbon group, an aromatic-aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferred and for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferred and for example, vinyl, 1-propenyl, allyl, isopropenyl, butenyl, isobutenyl and the like can be mentioned. As the "alkynyl group", a $C_{2-6}$ alkynyl group and the like are preferred and for example, ethynyl, propargyl, 1-propynyl and the like can be mentioned. As the "cycloalkyl group", a $C_{3-6}$ cycloalkyl group and the like are preferred and for example, cyclopropyl, cyclobutyl, cyclopentyl, cyclohexyl and the like can be mentioned. For example, the "aryl group" is preferably a $C_{6-14}$ aryl group and the like and for example, phenyl, 1-naphthyl, 2-naphthyl, biphenylyl, 2-anthryl and the like can be mentioned. Of these, a $C_{6-10}$ aryl group is preferred, and phenyl is particularly preferred. As the "aralkyl group", a $C_{7-20}$ aralkyl group is preferred and for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is preferred, and benzyl is particularly preferred. The "hydrocarbon group" may be substituted by a substituent selected from a halogen atom (a chlorine atom, a bromine atom, a fluorine atom, an iodine atom), an alkyl group having 1 to 6 carbon atoms and optionally substituted by one or more halogen atoms, an oxo group and the like.

In the "organic group having an aliphatic hydrocarbon group" constituting the $OR^2$ group or $OR^4$ group in the above-mentioned formula (I), plural "aliphatic hydrocarbon groups" may be present by branching and the like. When plural "aliphatic hydrocarbon groups" are present in the "organic group having an aliphatic hydrocarbon group", they may be the same or different.

In the "organic group having an aliphatic hydrocarbon group" for $R^2$ or $R^4$ in the above-mentioned formula (I), the lower limit of the total carbon number is preferably 5, more preferably 10, further preferably 12, still more preferably 14, especially preferably 16, and particularly preferably 20. On the other hand in the "organic group having an aliphatic hydrocarbon group" for $R^2$ or $R^4$, the upper limit of the total carbon number is preferably 200, more preferably 150, further preferably 120, still more preferably 100, especially preferably 80, particularly preferably 60, particularly further preferably 40, and most preferably 30. The higher the carbon number, the better the crystallinity of the compound represented by the formula (I) in a polar solvent becomes, even when the peptide chain is a long chain.

Specific preferred examples of the "$OR^2$" group or "$OR^4$" group include dodecyloxy, cetyl oxy, octadecyloxy, docosyloxy, docosyloxy-dodecyloxy, triacontyloxy and the like. The "$OR^2$" group or "$OR^4$" group is present in a total number of p or r (p is an integer of 1 to 4 and r is an integer of 0 to 4), p is preferably 2 or 3, and r is preferably an integer of 0 to 2.

Specific preferred examples of the substituent optionally present in ring A or ring B in the above-mentioned formula (I) include a $C_{1-6}$ alkoxy group (e.g., a $C_{1-4}$ alkoxy group such as methoxy, ethoxy, propoxy, isopropoxy, butoxy, isobutoxy, sec-butoxy, tert-butoxy and the like), a $C_{1-6}$ alkyl group optionally substituted by one or more halogens (e.g., a $C_{1-6}$ alkyl group such as methyl, ethyl, propyl, isopropyl, butyl, isobutyl, sec-butyl, tert-butyl, pentyl, hexyl and the like, a halogen-substituted $C_{1-6}$ alkyl group such as trifluoromethyl, trichloromethyl and the like), and a halogen atom. Of these, a $C_{1-6}$ alkoxy group is preferred.

A preferred embodiment of the anchor represented by the above-mentioned formula (I) is a compound of the formula (I), wherein
Y is a hydroxy group;
$R^1$ is a hydrogen atom;
$R^2$ and/or $R^4$ are/is an aliphatic hydrocarbon group having 5 to 60 carbon atoms;
p is an integer of 1 to 3; and
r is an integer of 0 to 2.

Another preferred embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an aliphatic hydrocarbon group having 5 to 60 carbon atoms; and
p is an integer of 1 to 3.

Another preferred embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an alkyl group having 10 to 40 carbon atoms; and
p is 2 or 3.

Another preferred embodiment of the anchor represented by the above-mentioned formula (I) is a compound of the formula (I), wherein
Y is a hydroxy group;
$R^a$, $R^b$, and $R^1$ are each a hydrogen atom;
$R^2$ is an alkyl group having 12 to 30 carbon atoms; and
p is 2 or 3.

Another preferred embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a benzyl group having 1 to 3 alkoxy groups having 12 to carbon atoms; and
p is an integer of 1 to 3.

Another preferred embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a cyclohexylmethyl group having 1 to 3 alkoxy groups having 12 to 30 carbon atoms; and
p is an integer of 1 to 3.

Preferred examples of the anchor soluble in halogenated solvents or ether solvents, insoluble in polar solvents and having a molecular weight of not less than 300 in the present invention include the following anchors.
3,4,5-tri(octadecyloxy)benzyl alcohol,
2,4-di(docosyloxy)benzyl alcohol,
4-methoxy-2-[3',4',5'-tri(octadecyloxy)benzyloxy]benzyl alcohol,
4-methoxy-2-[3',4',5'-tri(octadecyloxy)cyclohexylmethyloxy]benzyl alcohol,
2-methoxy-4-[3',4',5'-tri(octadecyloxy)cyclohexylmethyloxy]benzyl alcohol,
4-[3',4',5'-tri(octadecyloxy)cyclohexylmethyloxy]benzyl alcohol,
3,5-dimethoxy-4-[3',4',5'-tri(octadecyloxy)cyclohexylmethyloxy]benzyl alcohol,
2,4-di(dodecyloxy)benzyl alcohol,
3,4,5-tri(octadecyloxy)benzylamine,
bis(4-docosyloxyphenyl)methanol,
bis(4-docosyloxyphenyl)methylamine, and
2-(12-docosyloxy-dodecyloxy)-9-(3-fluorophenyl)-9-bromofluorene.

Other preferred examples of the pseudo-solid-phase protecting group include the following.
A branched chain-containing aromatic compound represented by the formula (II):

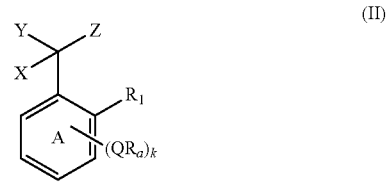

(II)

wherein
Q in the number of k is a single bond, or —O—, —S—, —C(=O)O—, —C(=O)NH— or —NH—;
$R_a$ in the number of k are each independently an organic group having at least one aliphatic hydrocarbon group having one or more branched chains, a total branched chain number of not less than 3, and a total carbon number of not less than 14 and not more than 300;
k is an integer of 1-4;
$R_1$ is a hydrogen atom, or when Z is a group represented by the following formula (a), shows a single bond together with $R_2$, and form a fluorene ring together with ring B;
ring A may have a substituent selected from the group consisting of $R_1$, $QR_a$ in the number of k, C(X)(Y)Z, a halogen atom, a $C_{1-6}$ alkyl group optionally substituted by one or more halogen atoms, and a $C_{1-6}$ alkoxy group optionally substituted by one or more halogen atoms;
X is a hydrogen atom or a phenyl group;
Y is a hydroxyl group or an —NHR group (R is a hydrogen atom, an alkyl group or an aralkyl group); and
Z is a hydrogen atom or a group represented by the formula (a):

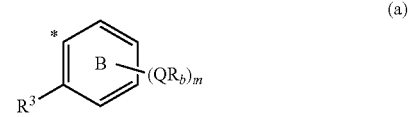

(a)

wherein * shows a binding site;
m is an integer of 0-4;
Q in the number of m is as defined above;
$R_b$ in the number of m are each independently an organic group having at least one aliphatic hydrocarbon group having one or more branched chains, a total branched chain number of not less than 3, and a total carbon number of not less than 14 and not more than 300;
$R_2$ is a hydrogen atom, or shows a single bond together with $R_1$, and form a fluorene ring together with ring A; and
ring B may have a substituent selected from the group consisting of $QR_b$ in the number of m, $R_2$, a halogen atom, a $C_{1-6}$ alkyl group optionally substituted by one or more halogen atoms, and a $C_{1-6}$ alkoxy group optionally substituted by one or more halogen atoms;
the organic group having at least one aliphatic hydrocarbon group having one or more branched chains, a total branched chain number of not less than 3, and a total carbon number of not less than 14 and not more than 300 for the aforementioned $R_a$ or $R_b$ is a group having three or more, the same or different divalent groups represented by the formula (b):

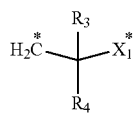

wherein * is a binding site with the adjacent atom;
$R_3$ and $R_4$ are each independently a hydrogen atom or a $C_{1-4}$ alkyl group; and
$X_1$ is a single bond, a $C_{1-4}$ alkylene group or an oxygen atom, provided that $R_3$ and $R_4$ are not hydrogen atoms at the same time).

More preferably, the following compound can be recited:
a branched chain-containing aromatic compound selected from the group consisting of
2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenyl-methaneamine;
3,4,5-tri(2',3'-dihydrophytyloxy)benzyl alcohol;
3,4,5-tri(2',3'-dihydrophytyloxy)benzylamine;
4-(2',3'-dihydrophytyloxy)benzylamine;
2-[3',4',5'-tri(2'',3''-dihydrophytyloxy)benzyloxy]-4-methoxybenzyl alcohol;
4-(2',3'-dihydrophytyloxy)-2-methoxybenzyl alcohol;
4-(2',3'-dihydrophytyloxy)-2-methoxybenzylamine;
4-(2',3'-dihydrophytyloxy)-2-methylbenzyl alcohol;
4-(2',3'-dihydrophytyloxy)-2-methylbenzylamine;
2,2,4,8,10,10-hexamethyl-5-dodecaneacid (4-hydroxymethyl)phenylamide;
4-(3,7,11-trimethyldodecyloxy)benzyl alcohol;
2-(3,7,11-trimethyldodecyloxy)-9-phenylfluoren-9-ol;
a compound represented by the formula:

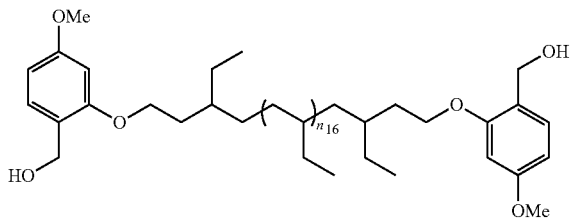

wherein $n_{16}$ is 23 or 34;
a compound represented by the formula:

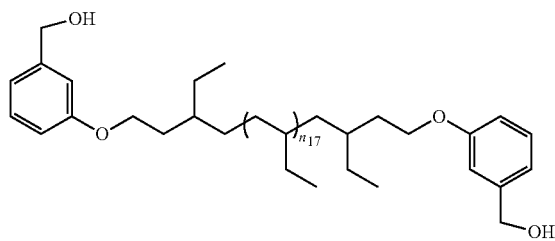

wherein $n_{17}$ is 23 or 34;
a compound represented by the formula:

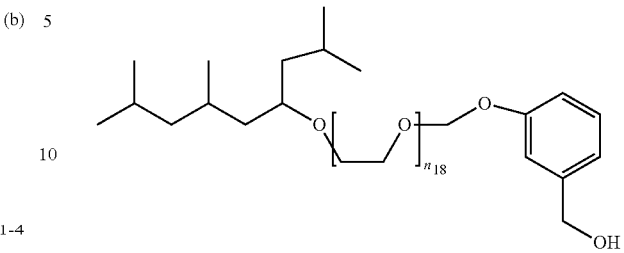

wherein $n_{18}$ is 5-7; and
a compound represented by the formula:

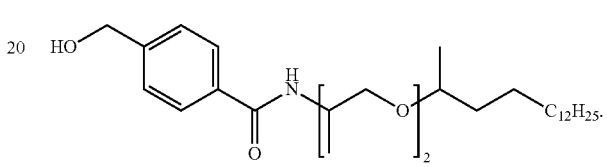

Other preferred pseudo-solid-phase protecting group includes di(4-docosoxyphenyl)methylamine ($NHCH_2(Phe(4-OC_{22}H_{45}))_2$) and the like.

While the production method of the aforementioned anchor is not particularly limited, it can be produced from a starting compound according to a method known per se (JP-A-2000-44493, WO 2006/104166, WO 2007/034812, WO 2007/122847, WO 2010/113939, WO 2010/104169, WO 2011/078295, WO 2012/029794, all of which are incorporated herein by reference in their entireties, and the like) or a method analogous thereto. A compound used as a starting compound, for example, halide corresponding to the group $R^2$ or $R^4$ in the formula (I) and the like can be obtained as a commercially available product or can be produced by a method known per se or a method analogous thereto.

Removal of the protecting group of functional groups other than the SH group of completely-protected peptide is explained below.

For the removal of the protecting groups in this step (1-A), a deprotecting method known per se can be adopted without particular limitation according to the kind of the protecting group to be removed. It is necessary to select conditions that do not adversely affect the protecting groups for the SH groups and the protection of SH groups by the formation of temporary S—S bonds. For example, deprotection is preferably performed in the absence of a reducing agent. Those of ordinary skill in the art can appropriately select suitable conditions according to the overall synthesis strategies.

For example, in the case of a lower alkyl group such as Me, Et or the like, it can be removed by reaction with a base such as sodium hydroxide, potassium hydroxide or the like in a solvent such as an aqueous organic solvent, a polar organic solvent or the like.

In the case of tBu, it can be removed by reaction with an acid such as trifluoroacetic acid (TFA), hydrochloric acid or the like in a solvent such as chloroform, ethyl acetate or the like.

In the case of Bzl, it can be removed by reaction in a solvent such as methanol, DMF or the like or with a strong acid such as hydrogen fluoride, trifluoromethanesulfonic acid, HBr or the like.

While the acid usable for the removal of a Boc group is not particularly limited, mineral acids such as hydrogen chloride, sulfuric acid, nitric acid and the like, carboxylic acids such as formic acid, trifluoroacetic acid (TFA) and the like, sulfonic acids such as methanesulfonic acid, p-toluenesulfonic acid and the like, or a mixture thereof can be used. As the mixture, for example, hydrogen bromide/acetic acid, hydrogen chloride/dioxane, hydrogen chloride/acetic acid and the like can be mentioned.

While the organic base usable for the removal of an Fmoc group is not particularly limited, secondary amines such as diethylamine, piperidine, morpholine and the like, tertiary amines such as diisopropylethylamine, dimethylaminopyridine, 1,8-diazabicyclo[5.4.0]-7-undecene (DBU), 1,4-diazabicyclo[2.2.2]octane (DABCO), 1,5-diazabicyclo[4.3.0]-5-nonene (DBN) and the like can be mentioned.

More preferably, the Fmoc group is removed by treating same with a non-nucleophilic organic base in a halogenated solvent or ether solvent. The deprotection is performed in a solvent that does not influence the reaction.

Examples of the non-nucleophilic base include 1,8-diazabicyclo[5.4.0]-7-undecene (DBU), 1,4-diazabicyclo[2.2.2]octane (DABCO), 1,5-diazabicyclo[4.3.0]-5-nonene (DBN) and the like. DBU and DBN are preferred, and DBU is more preferred.

Removal of pseudo-solid-phase protecting group is preferably performed by an acid treatment. As an acid to be used for the deprotection, trifluoroacetic acid (TFA), hydrochloric acid, sulfuric acid, methanesulfonic acid, p-toluenesulfonic acid and the like can be mentioned, with preference given to TFA. As a solvent to be used for the deprotection, for example, chloroform, dichloromethane, 1,2-dichloroethane or a mixed solvent thereof and the like can be mentioned. The concentration of an acid to be used for the deprotection is, for example, 0.1 w/v %-5 w/v %.

Removal of the pseudo-solid-phase protecting group may also be performed simultaneously with the removal of the protecting groups of other functional groups in the peptide. In this case, a conventional method used in the field, particularly peptide synthesis, is used, and a method including adding an acid and the like is preferably used. As the acid, trifluoroacetic acid (TFA), hydrochloric acid, sulfuric acid, mesylic acid, tosylic acid, trifluoroethanol, hexafluoroisopropanol and the like are used. Of these, TFA is particularly preferred. The amount of the acid to be used is appropriately set according to the kind of the acid to be used, and an amount suitable for removing the anchor group is used. The amount of the acid to be used is preferably not less than 3 mol, more preferably not less than 5 mol, preferably not more than 100 mol, more preferably not more than 50 mol, per 1 mol of the peptide. Along with such use, trifluoromethanesulfonic acid, trimethylsilyl trifluoromethanesulfonate, $BF_3$ etherate and the like can also be added as a further source of strong acid.

The conditions for the removal of the above pseudo-solid-phase protecting groups can be appropriately selected by those of ordinary skill in the art according to the kind of the protecting group to be used.

Other protecting groups can be appropriately removed according to the kind thereof by a method generally performed in the pertinent technical field, or according to the deprotection method of the protecting groups described in the present specification.

When the "S-protected peptide" obtained in the above-mentioned step (1-A) and step (1-B) is obtained under liquid phase conditions, it can be isolated and purified by a method conventionally used in the pertinent technical field, and is subjected to step (2). When the "S-protected peptide" is obtained under solid phase conditions, it is cut out from the solid phase carrier by a conventionally-used method, and subjected to step (2).

In the above, step (1-A) and step (1-B) have been explained. As mentioned above, in the present invention, the S-protected peptide of step (2) can be obtained by performing step (1-A) and step (1-B). The order of step (1-A) and step (1-B) is not limited to this order and can be appropriately changed according to the embodiments. Therefore, step (1-B) may be performed after step (1-A), step (1-A) may be performed after step (1-B), these may be combined, or the both steps may be performed simultaneously, all of these cases are encompassed in the scope of the present invention.

Therefore, step (1-A) and step (1-B) integrally constitute step (1) for producing the "S-protected peptide" used in the subsequent step (2). That is, the step (1) is a step for obtaining "S-protected peptide", including performing step (1-A) and step (1-B) in combination.

Step (2)

The step (2) is a step for obtaining a cyclized peptide by subjecting the "linear peptide having two or more SH groups as the functional groups on the peptide, in which all SH groups are protected by formation of a temporary S—S bond, and the protecting groups of all functional groups other than the SH group are removed (S-protected peptide)", which is obtained in step (1-A) and step (1-B), to a folding step under oxidation and reduction conditions to allow for re-formation of S—S bond in the peptide molecule.

In this step, the temporary S—S bond formed for the protection of the SH group by subjecting to the folding step is once cleaved, and the S—S bond is re-formed to construct a stable (natural type) higher-order structure, whereby a cyclized peptide of interest can be obtained.

In the folding step of this step, under oxidation and reduction conditions, cleavage by the reduction of its temporary S—S bond, formation of an S—S bond by oxidation, and an exchange reaction of S—S bond by re-cleavage by reduction of the formed S—S bond and by a re-formation by oxidation proceed sequentially in the "S-protected peptide", which eventually leads to a stable cyclized peptide (natural type when the cyclized peptide of interest is a naturally occurring substance) having a higher-order structure. Particularly, in the case of a peptide having 4 or more SH groups, there exist two or more kinds of combination of S—S bond formation between SH groups. In this step, one or more S—S bonds are formed between SH groups selected as being compatible to the stable higher-order structure. In conventional methods, it is necessary to take measures at the design stage of a linear peptide, such as protection in advance of SH groups by different protecting groups according to the combination of the SH groups for which an S—S bond is to be formed. However, in the present invention, a cyclized peptide of interest can be obtained more conveniently and efficiently.

The "oxidation and reduction conditions" in the present invention mean conditions under which cleavage by the reduction of its temporary S—S bond, formation of an S—S bond by oxidation, and an exchange reaction of S—S bond by re-cleavage by reduction of the formed S—S bond and by a re-formation by oxidation proceed sequentially in the "S-protected peptide", which eventually leads to a stable cyclized peptide (natural type when the cyclized peptide of interest is a naturally occurring substance) having a higher-order structure. In general, these are performed in the coexistence of an oxidant and a reducing agent. However, as described later, only a reducing agent is required and it is not essential to add an oxidant from the outside.

As the combination of the oxidant and the reducing agent used in this step, those generally used in the pertinent technical field can be utilized. Examples thereof include a combination of an oxidant and a reducing agent such as a combination of a disulfide-based reagent/thiol-based reagent, for example, cystine/cysteine, glutathione-oxidized form/glutathione-reduced form, cystamine/cysteamine, dithiodiethanol/β-mercaptoethanol and the like. Preferred embodiments of the combination of "oxidant and reducing agent" include combinations of cystine/cysteine, and glutathione-oxidized form/glutathione-reduced form.

As described above, oxygen dissolved in the solvent acts as an oxidant, and the temporary S—S bond itself existing in the S-protected peptide also acts as an oxidant. Therefore, an embodiment in which only a reducing agent is used without adding an oxidant from the outside is also included in the folding step under the oxidation and reduction conditions in step (2). When an oxidant is not added from the outside and dissolved oxygen or the temporary S—S bond itself present in the S-protected peptide functions as an oxidant, examples of the reducing agent include cysteine, glutathione-reduced form, cystamine, β-mercaptoethanol and the like (preferred is cysteine), though the reducing agent is not limited to these as long as it is generally used in the pertinent technical field.

While this step can be performed in a suitable solvent, it is preferably performed in a polar solvent (e.g., water, alcohol such as ethanol, etc.) or a mixed solvent thereof.

This step can be generally performed at pH 6 or higher (14 or lower), is preferably performed under basic conditions, for example, pH 7 or higher (14 or lower), more preferably pH 8 or higher (14 or lower), particularly preferably pH 8 or higher and 13 or lower.

This step can be performed according to the conditions under which the folding process is generally performed in the pertinent technical field.

The concentration of the "S-protected peptide" when performing the folding step is not particularly limited and can be appropriately determined by those skilled in the art according to the kind of the "S-protected peptide". For example, it can be performed in the general concentration range of folding of from 0.1 mg/ml to 1 mg/ml. As a result of consideration, it was confirmed that the desired cyclized peptide can be efficiently obtained even in a higher concentration range in the present invention since the SH group is protected by the temporary S—S bond formation. For example, the present step can also be performed in the range of not less than 1 mg/ml to 50 mg/ml, or not less than 1 mg/ml to 25 mg/ml, or not less than 1 mg/ml to 15 mg/ml.

The method for performing the folding step under other oxidation and reduction conditions can be appropriately selected by those of ordinary skill in the art according to the substrate peptide of interest and according to a method known in the pertinent technical field. For example, "PEPTIDE GOUSEI NO KISO TO JIKKEN, Maruzen Publishing Co., Ltd. (1985)", which is incorporated herein by reference in its entirety, and the like can also be referred to.

The basic embodiments of the present invention have been described above. Preferred embodiments are successively described below.

Step (1): [Step (1-A) and Step (1-B)]

Embodiment 1

The present invention can be performed by achieving the protection of all SH groups by forming a temporary S—S bond in step (1-B) by forming a temporary S—S bond with all SH groups within peptide molecules and/or between peptide molecules (temporary S—S formation).

In this embodiment, any one pair of SH groups in a linear peptide having two or more SH groups as the functional groups on the peptide are protected by intramolecular formation in a peptide and/or intermolecular formation in peptides of a temporary S—S bond, and a mixture of peptides crosslinked or linked by a temporary S—S bond (temporary S—S formed peptide mixture) can be obtained. Here, a mixture of peptides having various structures and linked by a temporary S—S bond is obtained. The mixture does not require particular purification or selection of a specific compound, and is useful because the whole mixture can be used in the next step.

Temporary S—S formation is performed in an appropriate combination with the protecting group of the SH group used in the peptide of interest and the method of forming a temporary S—S bond. Preferred embodiments are specifically described separately for each case.

Embodiment 1-1

In this embodiment, more specifically, S-protected peptide can be obtained by subjecting the completely-protected peptide to temporary S—S formation in step (1-B) to obtain a temporary S—S formed peptide mixture, and removing the protecting groups of all functional groups other than the SH group protected by temporary S—S bond formation in the temporary S—S formed peptide mixture in step (1-A).

In this embodiment, a preferred protecting group of the SH group in the completely-protected peptide is a protecting group other than S-type protecting group (described later). For example, a trityl group (Trt group), an acetamidomethyl group (Acm group), a benzyl group (Bzl group), a 4-methylbenzyl group (4-MeBzl group), and a 4-methoxybenzyl group (MBzl group) can be mentioned.

In this embodiment, the temporary S—S formation is performed, for example, by an iodine treatment, a thallium (III) trifluoroacetate treatment (Tl(OCOCF$_3$)$_3$ treatment), and the like. It is preferably performed by an iodine treatment.

Each treatment such as the above-mentioned iodine treatment and the like can be performed under the conditions generally performed in the pertinent technical field. For example, in the case of an iodine treatment, the completely-protected peptide is treated with iodine in a solvent such as chloroform, acetic acid, alcohol (e.g., methanol, etc.), hexafluoroisopropanol, and the like, or in a water-containing or mixture solvent thereof. Iodine is used, for example, at 0.3-8 equivalents, preferably 0.5-6 equivalents, relative to a peptide constitutional unit (1 mol) having an SH group. In another embodiment, iodine is used, for example, at 1-6 equivalents, preferably 1-3 equivalents, relative to a peptide constitutional unit (1 mol) having an SH group. In case the protecting group of the SH group is an acetamidomethyl group (Acm group), iodine is used at 1-10 equivalents, preferably 1-5 equivalents.

The temperature at the time of treatment is not particularly limited, and can be appropriately selected and carried out within the temperature range from cooling to heating according to the reaction. For example, the treatment can be performed at room temperature (normal temperature).

In temporary S—S formation, even when treated with other oxidant (thallium (III) trifluoroacetate, etc.), it can be performed under the similar equivalent relationship and temperature conditions.

The thallium (III) trifluoroacetate treatment is a method using thallium (III) trifluoroacetate (Tl(OCOCF$_3$)$_3$) as an oxidant. For example, it can be performed by treating a completely-protected peptide with the oxidant in trifluoroacetic acid (TFA).

In this embodiment, protecting groups for functional groups other than SH groups, conditions for deprotecting them, and the like can be performed with reference to those described above. Deprotection is preferably performed by treating with trifluoroacetic acid (TFA).

Embodiment 1-2

In this embodiment, more specifically, the S-protected peptide is obtained by removing the protecting groups of all functional groups other than the Sb group of the completely-protected peptide in step (1-A), and then or simultaneous subjecting the (said) peptide to temporary S—S formation in step (1-B) to obtain a temporary S—S formed peptide mixture.

In this embodiment, preferred examples of the protecting group for the SH group in the completely-protected peptide include the protecting group other than the S-type protecting group. For example, acetamidomethyl group (Acm group), t-butyl group (t-Bu group), trityl group (Trt group), benzyl group (Bzl group), 4-methylbenzyl group (4-MeBzl group), and 4-methoxybenzyl group (MBzl group) can be mentioned.

In this embodiment, the temporary S—S formation is performed, for example, by an iodine treatment, a DMSO/TFA (dimethyl sulfoxide/trifluoroacetic acid) treatment, a thallium(III) trifluoroacetate treatment (Tl(OCOCF$_3$)$_3$ treatment) and the like. It is preferably performed by an iodine treatment.

In this embodiment, the deprotection of step (1-A) and the temporary S—S formation of step (1-B) can also be performed simultaneously and, for example, they can be performed using a DMSO/TFA treatment. To be specific, 10% DMSO/TFA (DMSO:TFA=1:10) and the like can be used.

This treatment can be performed under the equivalent relationship and temperature conditions similar to those in the above-mentioned iodine treatment.

For the details of the iodine treatment and thallium(III) trifluoroacetate treatment, those mentioned above can be referred to.

The protecting groups for functional groups other than SH groups, conditions for deprotecting them, and the like can be performed with reference to those described above. Deprotection is preferably performed by treating with trifluoroacetic acid.

Embodiment 1-3

In this embodiment, more specifically, S-protected peptide can be obtained by
a)
1) after removing the protecting groups of all functional groups other than the SH group in step (1-A),
2) removing the protecting group of the SH group, and further
3) carrying out temporary S—S formation in step (1-B) to obtain a temporary S—S formed peptide mixture, or
b)
1) after removing the protecting group of the SH group of the completely-protected peptide,
2) carrying out temporary S—S formation in step (1-B) to obtain a temporary S—S formed peptide mixture, and further
3) removing the protecting groups of all functional groups other than the SH group protected by temporary S—S bond formation in the temporary S—S formed peptide mixture in step (1-A).

In this embodiment, a preferred protecting group of the SH group in the completely-protected peptide is a protecting group other than S-type protecting group. For example, a phenylacetamidomethyl group (Phacm group), a 4-methoxybenzyl group (MBzl group), and a mono methoxytrityl group (MMTrt group) can be mentioned.

The above-mentioned protecting groups can be appropriately removed according to the kind thereof by a method generally performed in the pertinent technical field, or according to the deprotection method of the protecting groups described in the present specification. In this embodiment, when the protecting group of the SH group is a phenylacetamidomethyl group (Phacm group), it is preferably removed by a treatment with an aqueous solution in the presence of penicillin amidohydrolase (PGA). When the protecting group of the SH group is a 4-methoxybenzyl group (MBzl group), it is preferably removed by a treatment with DDQ (dichlorodicyano benzoquinone). When the protecting group of the SH group is a mono methoxytrityl group (MMTrt group), it is preferably removed by a treatment with a weak acid (e.g., 1% TFA).

In this embodiment, the temporary S—S formation is performed, for example, by an iodine treatment, an Npys-OMe treatment (methyl 3-nitro-2-pyridinesulfenate treatment), a thallium(III) trifluoroacetate treatment (Tl (OCOCF$_3$)$_3$ treatment), and the like. It is preferably performed by an iodine treatment or an Npys-OMe treatment, more preferably an iodine treatment.

The Npys-OMe treatment (methyl 3-nitro-2-pyridine sulfenate treatment) is a method using Npys-OMe as an oxidant. For example, it can be performed by treating a completely-protected peptide with the oxidant in chloroform, DMF, acetonitrile, or a mixed solvent thereof.

This treatment can be performed under the equivalent relationship and temperature conditions similar to those in the above-mentioned iodine treatment.

For the details of the iodine treatment and thallium(III) trifluoroacetate treatment, those mentioned above can be referred to.

The protecting groups for functional groups other than SH groups, conditions for deprotecting them, and the like can be performed with reference to those described above. Deprotection is preferably performed by treating with trifluoroacetic acid (TFA).

Embodiment 2

The present invention can be performed by achieving the protection of all SH groups by forming a temporary S—S bond in step (1-B) by forming a temporary S—S bond with an S-type protecting group.

Embodiment 2-1

In this embodiment, more specifically, S-protected peptide can be obtained by
(1)
(i) re-protecting protecting groups of SH groups of a linear peptide having two or more SH groups as functional groups on the peptide, in which an N terminal amino group is optionally protected, and all of a C-terminal carboxy group and other functional groups on the peptide are protected, with an S-type protecting group, or (ii) protecting same with an S-type protecting group in advance to obtain a peptide in which all SH groups are protected by formation of a temporary S—S bond with the S-type protecting group in step (1-B), and (2) removing the protecting groups of all functional groups other than the SH group protected by the temporary S—S bond in the peptide in step (1-A).

A temporary S—S bond with an S-type protecting group can be formed by, for example, treating with a reagent for introducing an S-type protecting group, which is used in the pertinent technical field, such as 3-nitro-2-pyridinesulfenyl group (Npys group), t-butylmercapto group (S-tBu group), ethylmercapto group (S-Et group), and the like under conditions used generally. For example, when NpysCl is used as a reagent for introducing a 3-nitro-2-pyridinesulfenyl group (Npys group), the reaction can be performed in chloroform, DMF, acetonitrile, or a mixed solvent thereof.

The reagent for introducing an S-type protecting group is used, for example, at 1-6 equivalents, preferably 1-3 equivalents, relative to a peptide constitutional unit (1 mol) having an SH group (or protected SH group). The temperature at the time of treatment is not particularly limited, and can be appropriately selected and carried out within the temperature range from cooling to heating according to the reaction. For example, the treatment can be performed at room temperature (normal temperature).

The "re-protecting protecting groups of SH groups of a peptide with S-type protecting group" refers to an embodiment in which all SH groups in a peptide form a temporary S—S bond with an S-type protecting group by re-protecting the peptide in which SE groups are protected by a protecting group other than the S-type protecting group by a reagent for introducing an S-type protecting group. In this case, a 3-nitro-2-pyridinesulfenyl group (Npys group) is preferred as the S-type protecting group.

On the other hand, "protecting with an S-type protecting group in advance" refers to an embodiment in which a peptide starting material containing an SH group as a functional group (cysteine residue, homocysteine residue, 3-mercaptopropionyl group, etc.) is protected in advance by an S-type protecting group (e.g., t-butylmercapto group (S-tBu group), ethylmercapto group (S-Et group), 3-nitro-2-pyridinesulfenyl group (Npys group), etc.). In this case, a t-butylmercapto group (S-tBu group) is preferred as the S-type protecting group.

As the protecting group for the SH group in "re-protecting groups of SH groups of a peptide with S-type protecting group", a protecting group other than S-type protecting groups is used and, for example, a trityl group (Trt group) is used.

The protecting groups for respective functional groups other than SH groups, conditions for deprotecting them, and the like can be performed with reference to those described above. Deprotection is preferably performed by treating with trifluoroacetic acid (TFA).

The embodiments of steps (1-A) and (1-B) in step (1) of the present invention are described above. In addition, "the problem of a decrease in the yield by alkylation of the SH groups due to the debris of deprotected various kinds of protecting groups and the like, and further, a decrease in the yield of the desired peptide in the cyclization reaction due to the by-produced impurities" can be solved because protecting groups other than SH group are removed when an SH group in a peptide having the SH group as the functional group on the peptide is protected.

Furthermore, the efficiency of folding in step (2) can be enhanced by protecting SH group by the formation of a temporary S—S bond.

Step (2)

Embodiment 1

In this embodiment, the folding step of step (2) is performed in an aqueous solution at pH 6 or higher, and preferably performed under basic conditions, for example, pH 7 or higher (14 or lower), more preferably pH 8 or higher (14 or lower), particularly preferably pH 8 or higher and 13 or lower.

Embodiment 2

In this embodiment, the concentration of the "S-protected peptide" in the system in the folding step in step (2) is the general concentration range of folding of from 0.1 mg/ml to 1 mg/ml.

Embodiment 2-1

In this embodiment, the concentration of the "S-protected peptide" in the system in the folding step in step (2) is the general concentration range of not less than 1 mg/ml, for example, not less than 1 mg/ml to 50 mg/ml, or not less than 1 mg/ml to 25 mg/ml, or not less than 1 mg/ml to 15 mg/ml.

The embodiment of step (2) of the present invention is described above. It is highly advantageous in that the cyclization reaction can be performed at a higher concentration than the general folding conditions.

Even in the folding step of the present invention, in rare cases, a reagent used as the oxidation-reducing agent produces additional impurities S—S bonded to the peptide. In general methods, the by-produced impurities are multiple kinds of multimers having a large molecular weight. In the method of the present invention, even when additional impurities should be by-produced, they are not multimers having a large molecular weight and the kind thereof is single, which greatly reduces the subsequent purification load. Thus, step (2) of the present invention also has such great advantage.

Other preferred embodiments of the present invention from a general point of view are described.

When practicing the present invention, the number of SH groups contained in the S-protected peptide is two or more. In one preferred embodiment, the number of SH groups contained in the S-protected peptide is two.

In another preferred embodiment, the number of SH groups contained in the S-protected peptide is 4 or more, preferably an even number.

When practicing the present invention, the number of residues of constitutional units such as amino acids, amino acid analogs and the like constituting the S-protected peptide is not particularly limited. It is generally not less than 4 and not more than 100, preferably not less than 6 and not more than 80, more preferably not less than 8 and not more than 60.

When practicing the present invention, the kind of the cyclized peptide to be the target is not particularly limited, and it may be, for example, a pharmaceutical product. In addition, it may be a naturally occurring substance, or a non-naturally occurring substance. Examples of such cyclized peptide include, but are not limited to, somatostatin, octreotide, atosiban, linaclotide, plecanatide, ziconotide, insulin detemir, insulin glulisine, and the like.

When practicing the present invention, one that can be led to a cyclized peptide having a stable (natural type when the cyclized peptide of interest is a naturally occurring substance) higher-order structure is preferably the target in the folding step under the oxidation and reduction conditions of the present invention.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless otherwise specified. In the present specification, when amino acid and the like are indicated by abbreviations, each indication is based on the abbreviation of the IUPAC-IUB Commission on Biochemical Nomenclature or conventional abbreviations in the art.

When an equivalent amount is indicated for the reagent used, it means an equivalent amount based on a series peptide product (e.g., completely-protected series peptide A product) as a starting material.

Production Example 1: Completely-Protected Series Peptide a Product

Using Fmoc-Tyr(tBu)-OH, Fmoc-Cys(Trt)-OH, Fmoc-Gly-OH, Fmoc-Thr(tBu)-OH, Fmoc-Ala-OH, Fmoc-Pro-OH, Fmoc-Asn(Trt)-OH, Fmoc-Glu(OtBu)-OH as starting materials, and 3,4,5-tri(2',3'-dihydrophytyloxy)benzyl alcohol (indicated as HO-Bzl(3,4,5-OPhy)) as a pseudo-solid-phase protecting group, a completely-protected series peptide A product having the following sequence was synthesized according to a conventional method (see WO 2012/029794; Angew Chem. Int. Ed. 2017. 27, (56), 7803, which are incorporated herein by reference in their entireties). In the present specification, the "completely-protected peptide" is a concept including both a protected N terminal amino group and a non-protected N terminal amino group. Thus, a peptide with non-protected N-terminal is also indicated as a "completely-protected series peptide product". The N-terminal Fmoc group of the following peptide was cleaved with a base according to a conventional method.
Completely-Protected Series Peptide A Product
H-Cys(Trt)-Cys(Trt)-Glu(OtBu)-Tyr(tBu)-Cys(Trt)-Cys(Trt)-Asn(Trt)-Pro-Ala-Cys(Trt)-Thr(tBu)-Gly-Cys(Trt)-Tyr(tBu)-OBzl (3,4,5-OPhy)

Production Example 2: Completely-Protected Series Peptide B Product

Using 3-mercapto(Trt)propionic acid, Fmoc-O-Ethyl-D-Tyr-OH, Fmoc-Ile-OH, Fmoc-Thr(tBu)-OH, Fmoc-Asn(Trt)-OH, Fmoc-Cys(Trt)-OH, Fmoc-Pro-OH, Fmoc-Orn(Boc)-OH, Fmoc-Gly-OH as starting materials, and 3,4,5-tri(2',3'-dihydrophytyloxy)benzyl alcohol (indicated as HO-Bzl(3,4,5-OPhy)) as a pseudo-solid-phase protecting group, a completely-protected series peptide B product having the following sequence was synthesized according to a conventional method (see WO 2012/029794; Angew Chem. Int. Ed. 2017. 27, (56), 7803, which are incorporated herein by reference in their entireties).

Completely-Protected Series Peptide B Product:
3-mercapto(Trt)propionyl-O-Ethyl-D-Tyr-Ile-Thr(tBu)-Asn(Trt)-Cys (Trt)-Pro-Orn(Boc)-Gly-OBzl(3,4,5-OPhy)

Production Example 3: Completely-Protected Series Peptide A' Product

Using Fmoc-Tyr(tBu)-OH, Fmoc-Cys(Trt)-OH, Fmoc-Gly-OH, Fmoc-Thr(tBu)-OH, Fmoc-Ala-OH, Fmoc-Pro-OH, Fmoc-Asn(Trt)-OH, Fmoc-Glu(OtBu)-OH as starting materials, and Alko-PEG Resin (Wang-PEG resin manufactured by WATANABE CHEMICAL INDUSTRIES, LTD.) as a solid phase protecting group, a completely-protected peptide A' having the following sequence was synthesized according to a conventional method. In the present specification, the "completely-protected peptide" is a concept including both a protected N terminal amino group and a non-protected N terminal amino group. Thus, a peptide with non-protected N-terminal is also indicated as a "completely-protected series peptide product". The N-terminal Fmoc group of the following peptide was cleaved with a base according to a conventional method.
Completely-Protected Series Peptide A' Product:
H-Cys(Trt)-Cys(Trt)-Glu(OtBu)-Tyr(tBu)-Cys(Trt)-Cys(Trt)-Asn(Trt)-Pro-Ala-Cys(Trt)-Thr(tBu)-Gly-Cys(Trt)-Tyr(tBu)-Alko-PEG Resin

Example 1: Temporary S—S Formation Route by Iodine Oxidation (Folding Concentration: 1 mg/ml)

The completely-protected series peptide A product (100 mg) was dissolved in chloroform (3.4 ml) and MeOH (methanol) (0.6 ml), and iodine (3 equivalents, 17.2 mg) was added. After the reaction, the mixture was partitioned twice with an aqueous solution of ascorbic acid (39.7 mg) dissolved in water (3.4 ml), and washed twice with 20% NaCl (sodium chloride) aqueous solution. The obtained organic layer was concentrated and dried by an evaporator. The solid was deprotected by adding to a mixed solution of TFA (trifluoroacetic acid) (0.975 ml), water (0.025 ml), and p-cresol (2 equivalents, 24.4 mg). IPE (isopropyl ether) (5 ml) was added and the precipitate was collected by filtration and dried to give a deprotected, temporary S—S formed peptide mixture (67.7 mg).

To a mixed solution of water (1 ml), EtOH (ethanol) (1 ml), cystine (1.0 mg), and cysteine (0.3 mg) was added 2.0 mg of the deprotected, temporary S—S formed peptide mixture obtained above, and aqueous ammonia (3 μl) was added to adjust the pH to 9.8. After 6 hr, the reaction mixture was analyzed by HPLC, and it was confirmed that 0.6 mg of cyclized peptide A having the following structure was produced at a purity of 82% (yield 52% vs completely-protected series peptide A product).
Elution Condition
elution time: 4.05 min
instrument used: WATERS ACQUITY UPLC
column: BEH Shield RP18 1.7 μm 2.1×100 mm
temperature: 40° C.
flow rate: 0.30 ml/min
mobile phase: SOLUTION A; 0.05% TFA/$H_2O$ SOLUTION B; 0.05%
TFA/MeCN(20)THF(80)
time program (SOLUTION A ratio)
0.00-0.05 min 99%
0.05-13.00 min 99-1%

Cyclized Peptide A:

H-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$-OH (S—S bond between Cys$^1$ and Cys$^6$, Cys$^2$ and Cys$^{10}$, Cys$^5$ and Cys$^{13}$) (SEQ ID NO: 1)

m/z[M+H]$^+$ 1526.3

Example 2: Temporary S—S Formation Route by Iodine Oxidation (Folding Concentration: 4 mg/ml)

To a mixed solution of water (1 ml), EtOH (1 ml), cystine (1.0 mg), and cysteine (0.3 mg) was added 8.0 mg of the deprotected, temporary S—S formed peptide mixture obtained in the above-mentioned Example 1, and aqueous ammonia (6 μl) was added to adjust the pH to 9.3. After 6 hr, the reaction mixture was analyzed by HPLC, and it was confirmed that 2.2 mg of cyclized peptide A was produced at a purity of 81% (yield 54% vs completely-protected series peptide A product).

Example 3: Temporary S—S Formation Route by Iodine Oxidation (Folding Concentration: 10 mg/ml)

To a mixed solution of water (1 ml), EtOH (1 ml), cystine (1.0 mg), and cysteine (0.3 mg) was added 20.0 mg of the deprotected, temporary S—S formed peptide mixture obtained in the above-mentioned Example 1, and aqueous ammonia (6 μl) was added to adjust the pH to 9.8. After 6 hr, the reaction mixture was analyzed by HPLC, and it was confirmed that 4.9 mg of cyclized peptide A was produced at a purity of 72% (yield 48% vs completely-protected series peptide A product).

Example 4: Temporary S—S Formation Route by 10% DMSO Oxidation/TEA Deprotection (Folding Concentrating: 1 mg/ml)

The completely-protected series peptide a product (50 mg) was added to a mixed solution of TFA (1.0 ml) and DMSO (dimethyl sulfoxide) (0.1 ml), and the mixture was deprotected at room temperature for 5 hr. IPE (5 ml) was added and the precipitate was collected by filtration and dried to give a deprotected, temporary S—S formed peptide mixture (19.4 mg).

To a mixed solution of water (1.0 ml), EtOH (1.0 ml), cystine (1.0 mg), and cysteine (0.3 mg) was added 2.0 mg of the deprotected, temporary S—S formed peptide mixture obtained above, and aqueous ammonia (3 μl) was added to adjust the pH to 9.5. After 5 hr, the reaction mixture was analyzed by HPLC, and it was confirmed that cyclized peptide A (0.9 mg) was produced at a purity of 81% (yield 48% vs completely-protected series peptide A product).

Example 5: Temporary S—S Bond Formation Route by S-Type Protecting Group, Npys Group (Folding Concentration: 1 mg/ml)

The completely-protected series peptide A product (100 mg) was dissolved in chloroform (3.4 ml) and MeOH (methanol) (0.6 ml), and Npys-Cl (3-nitro-2-pyridinesulfenyl chloride) (6 equivalents, 25.8 mg) was added. After the reaction, the mixture was partitioned twice with an aqueous solution of ascorbic acid (39.7 mg) dissolved in water (3.4 ml), and washed twice with 20% NaCl aqueous solution. The obtained organic layer was concentrated and dried by an evaporator. The solid was deprotected by adding to a mixed solution of TFA (1.95 ml), water (0.05 ml), and p-cresol (10 equivalents, 24.4 mg). IPE (10 ml) was added and the precipitate was collected by filtration and dried to give a deprotected, S-type protecting group, Npys group-protected peptide (84.7 mg).

To a mixed solution of water (1 ml), EtOH (1 ml), cystine (1.0 mg), and cysteine (0.3 mg) was added 2.0 mg of the deprotected, S-type protecting group, Npys group-protected peptide obtained above, and aqueous ammonia (3 μl) was added to adjust the pH to 9.8. After 2 hr, the reaction mixture was analyzed by HPLC, and it was confirmed that 0.8 mg of cyclized peptide A was produced at a purity of 73% (yield 56% vs completely-protected series peptide A product).

Example 6: Temporary S—S Formation Route by Iodine Oxidation (Folding Concentration: 10 mg/ml)

The completely-protected series peptide A' product (137 mg) was dissolved in chloroform (3.4 ml) and MeOH (0.6 ml), iodine (3 equivalents, 17.2 mg, 0.068 mmol) was added, and the mixture was stirred at room temperature for 2 hr. After the reaction, the mixture was partitioned twice with an aqueous solution of ascorbic acid (39.7 mg) dissolved in water (3.4 ml), and washed twice with 20% NaCl aqueous solution (3.4 ml). The obtained organic layer was concentrated and dried by an evaporator. The solid was deprotected at room temperature for 5 hr by adding to a mixed solution of TFA (1.95 ml), water (0.05 ml), and p-cresol (10 equivalents, 24.4 mg). The resin was washed with TFA (2 ml) by filtration, IPE (10 ml) was added to the filtrate, and the precipitate was collected by filtration and dried to give a deprotected, temporary S—S formed peptide mixture (34.5 mg).

To a mixed solution of water (1.7 ml), EtOH (1.7 ml), cystine (1.7 mg), cysteine (0.6 mg) was added 34.5 mg of the deprotected, temporary S—S formed peptide mixture obtained above, aqueous ammonia (60 μl) was added to adjust the pH to 9.2, and the mixture was stirred at room temperature. After 1 hr, the reaction mixture was analyzed by HPLC, and it was confirmed that 17 mg of cyclized peptide A was produced at a purity of 68% (yield 49% vs completely-protected series peptide A' product).

Example 7: Temporary S—S Formation Route by Iodine Oxidation (Folding Concentration: 1 mg/ml)

The completely-protected series peptide B product (1.0 g) was dissolved in CPME (cyclopentylmethylether) (16.8 ml) and MeOH (4.2 ml), and iodine (1 equivalent, 48.4 mg) was added. After the reaction, the mixture was partitioned twice with an aqueous solution of ascorbic acid (671 mg) dissolved in water (21 ml), and washed twice with 20% NaCl aqueous solution. The obtained organic layer was concentrated and dried by an evaporator to give a solid (894 mg).

The solid (300 mg) was deprotected by adding to a mixed solution of TFA (5.85 ml), water (0.25 ml) and p-cresol (10 equivalents, 150 mg). IPE (24 ml) was added and the precipitate was collected by filtration and dried to give a deprotected, temporary S—S formed peptide mixture.

To a mixed solution of water (1 ml), EtOH (1 ml), cystine (1.0 mg), and cysteine (0.3 mg) was added the deprotected, temporary S—S formed peptide mixture (2.0 mg) obtained above, and aqueous ammonia (3 μl) was added to adjust the pH to 9.8. After 6 hr, the reaction mixture was analyzed by HPLC and it was confirmed that cyclized peptide B was produced at a purity of 85%.

Elution Condition
elution time: 4.90 min
instrument used: WATERS ACQUITY UPLC
column: BEH Shield RP18 1.7 μm 2.1×100 mm
temperature: 40° C.
flow rate: 0.30 ml/min
mobile phase: SOLUTION A; 0.05% TFA/H$_2$O SOLUTION B; 0.05%
TFA/MeCN (20) THF (80)
time program (SOLUTION A ratio)
0.00-0.05 min 99%
0.05-13.00 min 99-1%
Cyclized Peptide B:
  3-mercaptopropionyl-O-Ethyl-D-Tyr-Ile-Thr-Asn-Cys-Pro-Orn-Gly-NH$_2$
  (S—S bond between 3-mercaptopropionyl and Cys)
  m/z[M+H]$^+$ 994.4

Example 8: Temporary S—S Formation Route by Iodine Oxidation (Folding Concentration: 6.5 mg/ml)

To a mixed solution of water (1 ml), EtOH (1 ml), cystine (1.0 mg), and cysteine (0.3 mg) was added the deprotected, temporary S—S formed peptide mixture (13.0 mg) obtained in the above-mentioned Example 7, and aqueous ammonia (3 μl) was added to adjust the pH to 8.9. After 1 hr, the reaction mixture was analyzed by HPLC and it was confirmed that cyclized peptide B was produced at a purity of 77%.

Comparative Example 1: Conventional Route (Folding Concentration: 1 mg/ml)

The completely-protected series peptide A product (6.00 g) was added to a mixed solution of TFA (114 ml), water (3 ml), TIPS (triisopropyl silane) (3 ml) and 3-mercaptopropionic acid (10 equivalents, 1.44 g), and the mixture was deprotected at 10° C. for 5 hr. IPE (600 ml) was added and the precipitate was collected by filtration and dried to give a series peptide A product.

To a mixed solution of water (1.0 ml), EtOH (1.0 ml), cystine (1.0 mg), and cysteine (0.3 mg) was added the series peptide A product (2.0 mg) obtained above, aqueous ammonia (3 μl) was added to adjust the pH to 10.0, and the mixture was stirred at room temperature. After 1 hr, the reaction mixture was analyzed by HPLC, and it was confirmed that cyclized peptide A (0.6 mg) was produced at a purity of 72% (yield 39% vs completely-protected series peptide A product).

Comparative Example 2: Conventional Route (Folding Concentration: 10 mg/ml)

To a mixed solution of water (1.0 ml), EtOH (1.0 ml), cystine (1.0 mg), and cysteine (0.3 mg) was added the series peptide A product (20 mg) obtained in the above-mentioned Comparative Example 1, aqueous ammonia (3 μl) was added to adjust the pH to 9.1, and the mixture was stirred at room temperature. After 1 hr, the reaction mixture was analyzed by HPLC, and it was confirmed that cyclized peptide A (0.4 mg) was produced at a purity of 8% (yield 2% vs completely-protected series peptide A product).

Comparative Example 3: Conventional Route (Folding Concentration: 1 mg/ml)

The completely-protected series peptide B product (1.0 g) was deprotected by adding to a mixed solution of TFA (7.60 ml), water (0.20 ml), triisopropyl silane (0.20 ml), 3-mercaptopropionic acid (10 equivalents, 405 mg) and p-cresol (10 equivalents, 412 mg). IPE (40 ml) was added and the precipitate was collected by filtration and dried to give a series peptide B product.

To a mixed solution of water (1 ml), EtOH (1 ml), cystine (1.0 mg), and cysteine (0.3 mg) was added the series peptide B product (2.0 mg) obtained above, and aqueous ammonia (3 μl) was added to adjust the pH to 9.7. After 6 hr, the reaction mixture was analyzed by HPLC, and it was confirmed that cyclized peptide B was produced at a purity of 61%.

Comparative Example 4: Conventional Route (Folding Concentration: 6.5 mg/ml)

To a mixed solution of water (1 ml), EtOH (1 ml), cystine (0.3 mg), and cysteine (0.1 mg) was added the series peptide B product (13.0 mg) obtained in the above-mentioned Comparative Example 3, and aqueous ammonia (3 μl) was added to adjust the pH to 9.6. After 6 hr, the reaction mixture was analyzed by HPLC, and it was confirmed that cyclized peptide B was produced at a purity of 17%.

Comparative Example 5: Conventional Route (Folding Concentration: 10 mg/ml)

The completely-protected series peptide A' product (67.8 mg) was added to a mixed solution of TFA (1.9 ml), water (50 μl), triisopropyl silane (50 μl) and 3-mercaptopropionic acid (100 equivalents, 240 mg), and the mixture was deprotected at room temperature for 5 hr. The resin was washed with TFA (2 ml) by filtration, IPE (20 ml) was added to the filtrate, and the precipitate was collected by filtration and dried to give a series peptide A product (15.6 mg).

To a mixed solution of water (0.5 ml), EtOH (0.5 ml), cystine (5.0 mg), and cysteine (0.2 mg) was added the series peptide A product (10.0 mg) obtained above, aqueous ammonia (3 μl) was added to adjust the pH to 9.5, and the mixture was stirred at room temperature. After 1 hr, the reaction mixture was analyzed by HPLC, and it was confirmed that cyclized peptide A (2.4 mg) was produced at a purity of 23% (yield 21% vs completely-protected series peptide A' product).

Example 9: Folding by Reducing Agent Alone (Folding Concentration: 2 mg/ml)

To a mixed solution of water (1 ml), EtOH (1 ml), and cysteine (0.3 mg) was added 4.0 mg of the deprotected, temporary S—S formed peptide mixture obtained in the above-mentioned Example 1, and aqueous ammonia (3 μl) was added to adjust the pH to 9.9. After 6 hr, the reaction mixture was analyzed by HPLC, and it was confirmed that 3.1 mg of cyclized peptide A was produced at a purity of 77.8% (yield 77% vs completely-protected series peptide A product).

Example 10: Folding by Different Oxidant/Reducing Agent (Folding Concentration: 1 mg/ml)

To a mixed solution of water (1 ml), EtOH (1 ml), glutathione oxidized form (6.0 mg) and glutathione reduced form (2.0 mg) was added 2.0 mg of the deprotected, temporary S—S formed peptide mixture obtained in the above-mentioned Example 1, and aqueous ammonia (3 μl) was added to adjust the pH to 9.3. After 1 hr, the reaction mixture was analyzed by HPLC, and it was confirmed that 0.9 mg of cyclized peptide A was produced at a purity of 65.0% (yield 56% vs completely-protected series peptide A product).

Production Example 4: Completely-Protected Series Peptide A" Product

Using Fmoc-Tyr(tBu)-OH, Fmoc-Cys(S-tBu)-OH, Fmoc-Gly-OH, Fmoc-Thr(tBu)-OH, Fmoc-Ala-OH, Fmoc-Pro-OH, Fmoc-Asn(Trt)-OH, Fmoc-Glu(OtBu)-OH as starting materials, and Alko-PEG Resin (Wang-PEG resin manufactured by WATANABE CHEMICAL INDUSTRIES, LTD.) as a solid phase protecting group, a completely-protected series peptide A" product having the following sequence was synthesized according to a conventional method. The N-terminal Fmoc group of the following peptide was cleaved with a base according to a conventional method.
Completely-Protected Series Peptide A" Product:
H-Cys(S-tBu)-Cys(S-tBu)-Glu(OtBu)-Tyr(tBu)-Cys(S-tBu)-Cys(S-tBu)-Asn(Trt)-Pro-Ala-Cys(S-tBu)-Thr(tBu)-Gly-Cys(S-tBu)-Tyr(tBu)-Alko-PEG Resin Example 11: Temporary S—S Bond Formation Route by S-Type Protecting Group (Folding Concentration: 1 mg/ml)

The completely-protected series peptide A" product (160 mg) was deprotected by adding to a mixed solution of TFA (2.59 ml), water (66.5 µl), and p-cresol (10 equivalents, 32.4 mg). IPE (30 ml) was added and the precipitate was collected by filtration and dried to give the following series peptide A" product (48.6 mg).
Series Peptide A" Product:
H-Cys(S-tBu)-Cys(S-tBu)-Glu-Tyr-Cys(S-tBu)-Cys(S-tBu)-Asn-Pro-Ala-Cys(S-tBu)-Thr-Gly-Cys(S-tBu)-Tyr-OH To a mixed solution of water (1 ml), EtOH (1 ml), and cysteine (10 mg) was added the series peptide A" product (2.0 mg) obtained above, and aqueous ammonia (2 µl) was added to adjust the pH to 9.3. After 16 hr, the reaction mixture was analyzed by HPLC, and it was confirmed that 1.0 mg of cyclized peptide A was produced at a purity of 52.2% (yield 51% vs series peptide A" product).
Elution Condition
elution time: 4.10 min
instrument used: WATERS ACQUITY UPLC
column: BEH Shield RP18 1.7 µm 2.1×100 mm
temperature: 40° C.
flow rate: 0.30 ml/min
mobile phase: SOLUTION A; 0.05% TFA/$H_2O$ SOLUTION B; 0.05%
TFA/MeCN(20)THF(80)
time program (SOLUTION A ratio)
0.00-0.05 min 99%
0.05-13.00 min 99-1%

Example 12: Removal of SH Protecting Group/Temporary S—S Formation Route by Iodine Oxidation (Folding Concentration: 1 mg/ml)

Selective removal of S-tBu group was performed by adding the completely-protected series peptide A" product (160 mg) to a mixed solution of water (2 ml), DTT (dithiothreitol) (60 equivalents, 278 mg), and aqueous ammonia (3 µL). The resin was washed by filtration to give the selective deprotected product. The selective deprotected product was dissolved in a mixed solution of chloroform (1.7 ml) and methanol (0.3 ml), and iodine (12 equivalents, 91.4 mg) was added. After the reaction, the resin was washed by filtration. The solid was deprotected by adding to a mixed solution of TFA (2.59 ml), water (66.5 ml), and p-cresol (32.4 mg). IPE (20 ml) was added and the precipitate was collected by filtration and dried to give a deprotected, temporary S—S formed peptide mixture (45.6 mg).

To a mixed solution of water (1 ml), EtOH (1 ml), cystine (0.3 mg), and cysteine (0.3 mg) was added the deprotected, temporary S—S formed peptide mixture (2.0 mg) obtained above, and aqueous ammonia (3 µl) was added to adjust the pH to 9.5. After 20 hr, the reaction mixture was analyzed by HPLC and it was confirmed that 1.6 g of cyclized peptide A was produced at a purity of 73% (yield 80% vs deprotected, temporary S—S formed peptide mixture).

Example 13: Temporary S—S Formation Route by Thallium Trifluoroacetate Oxidation (Folding Concentration: 1 mg/ml)

The completely-protected series peptide A product (50 mg) was dissolved in chloroform (0.85 ml) and the MeOH (0.05 ml), and thallium (III) trifluoroacetate (6 equivalents, 36.8 mg) was added. After the reaction, the mixture was partitioned twice with 20% NaCl aqueous solution. The obtained organic layer was concentrated and dried by an evaporator. The solid was deprotected by adding to a mixed solution of TFA (0.975 ml), water (0.025 ml), and p-cresol (24.4 mg). IPE (20 ml) was added and the precipitate was collected by filtration and dried to give a deprotected, temporary S—S formed peptide mixture (30.1 mg).

To a mixed solution of water (1 ml), EtOH (1 ml), cystine (0.3 mg), and cysteine (0.3 mg) was added the deprotected, temporary S—S formed peptide mixture (2.0 mg) obtained above, and aqueous ammonia (3 µl) was added to adjust the pH to 9.4. After 4 hr, the reaction mixture was analyzed by HPLC and it was confirmed that 1.3 g of cyclized peptide A was produced at a purity of 76% (yield 91% vs completely-protected series peptide A product).

Production Example 5: Completely-Protected Series Peptide A'" Product

Using Fmoc-Tyr(tBu)-OH, Fmoc-Cys(Acm)-OH, Fmoc-Gly-OH, Fmoc-Thr(tBu)-OH, Fmoc-Ala-OH, Fmoc-Pro-OH, Fmoc-Asn(Trt)-OH, Fmoc-Glu(OtBu)-OH as starting materials, and Alko-PEG Resin (Wang-PEG resin manufactured by WATANABE CHEMICAL INDUSTRIES, LTD.) as a solid phase protecting group, a completely-protected series peptide A'" product having the following sequence was synthesized according to a conventional method. The N-terminal Fmoc group of the following peptide was cleaved with a base according to a conventional method.
Completely-Protected Series Peptide A'" Product:
H-Cys(Acm)-Cys(Acm)-Glu(OtBu)-Tyr(tBu)-Cys(Acm)-Cys(Acm)-Asn(Trt)-Pro-Ala-Cys(Acm)-Thr(tBu)-Gly-Cys(Acm)-Tyr(tBu)-Alko-PEG Resin Example 14: Final Deprotection/Temporary S—S Formation Route (Folding Concentration: 1 mg/ml)

The completely-protected series peptide A'" product was deprotected by adding to a mixed solution of TFA (2.85 ml), water (75 µl), and TIPS (75 µl). IPE (30 ml) was added and the precipitate was collected by filtration and dried to give 108 mg of a series peptide A''' product having the following sequence.
Series Peptide A''' Product:
H-Cys(Acm)-Cys(Acm)-Glu-Tyr-Cys(Acm)-Cys(Acm)-Asn-Pro-Ala-Cys(Acm)-Thr-Gly-Cys(Acm)-Tyr-OH The series peptide A''' product (10 mg) was dissolved in a mixed solution of acetic acid (800 μL) and water (200 μL), and iodine (24 equivalents, 10.4 mg) was added. After 16 hr of the reaction, residual iodine was extracted 10 times with chloroform (1 ml). The obtained aqueous layer was concentrated by an evaporator, IPE was added, and the precipitate was collected by filtration and dried to give a deprotected, temporary S—S formed peptide mixture.

To a mixed solution of water (1 ml), EtOH (1 ml), cystine (0.1 mg), and cysteine (0.1 mg) was added the deprotected, temporary S—S formed peptide mixture (2.0 mg) obtained above, and aqueous ammonia (3 μl) was added to adjust the pH to 9.75. After 16 hr, the reaction mixture was analyzed by HPLC and it was confirmed that 1.4 g of cyclized peptide A was produced at a purity of 72% (yield 70% vs deprotected, temporary S—S formed peptide mixture).

Production Example 6: Completely-Protected Series Peptide C Product

Using Fmoc-Arg(Pbf)-OH, Fmoc-Gly-OH, Fmoc-Asn(Trt)-OH, Fmoc-Cys(Trt)-OH, Emoc-Ala-OH, Fmoc-Tyr(tBu)-OH, Fmoc-His(Trt)-OH, Fmoc-Lys(Boc)-OH, Fmoc-Gln(Trt)-OH, Fmoc-Ile-OH, Fmoc-Trp(Boc)-OH, Fmoc-Thr(tBu)-OH, Fmoc-NH-SAL-PEG Resin as solid phase protecting groups, a completely-protected peptide C having the following sequence was synthesized according to a conventional method. The N-terminal Fmoc group of the following peptide was cleaved with a base according to a conventional method.
Completely-Protected Series Peptide C Product:
H-Arg(Pbf)-Gly-Asn(Trt)-Cys(Trt)-Ala-Tyr(tBu)-His(Trt)-Lys(Boc)-Gly-Gln(Trt)-Ile-Ile-Trp(Boc)-Cys(Trt)-Thr(tBu)-Tyr(tBu)-His(Trt)-NH-SAL-PEG Resin Example 15: Temporary S—S Formation Route by Iodine Oxidation (Folding Concentration: 1 mg/ml)

The completely-protected series peptide C product (409 mg) was dissolved by mixing with chloroform (13.6 ml) and MeOH (2.4 ml), and iodine (1.5 equivalents, 9.5 mg) was added. After the reaction, the mixture was partitioned twice with an aqueous solution of ascorbic acid (44.0 mg) dissolved in water (16.0 ml), and washed twice with 20% NaCl aqueous solution. The obtained organic layer was concentrated and dried by an evaporator. The solid was deprotected by adding to a mixed solution of TFA (8.39 ml), water (0.21 ml), and p-cresol (27.0 mg). IPE (20 ml) was added and the precipitate was collected by filtration and dried to give a deprotected, temporary S—S formed peptide mixture (30.1 mg).

To a mixed solution of water (1.5 ml), EtOH (1.5 ml), cystine (0.3 mg), and cysteine (0.9 mg) was added the deprotected, temporary S—S formed peptide mixture (3.0 mg) obtained above, and aqueous ammonia (3 μl) was added to adjust the pH to 9.0. After 3 hr, the reaction mixture was analyzed by HPLC and it was confirmed that cyclized peptide C was produced at a purity of 56%.
Elution Condition
elution time: 3.78 min
instrument used: WATERS ACQUITY UPLC
column: BEH Shield RP18 1.7 jam 2.1×100 mm
temperature: 40° C.
flow rate: 0.30 ml/min
mobile phase: SOLUTION A; 0.05% TFA/H$_2$O SOLUTION B; 0.05% TFA/MeCN(20)THF(80)
time program (SOLUTION A ratio)
0.00-0.05 min 99%
0.05-13.00 min 99-1%
Cyclized Peptide C:
H-Arg$^1$-Gly$^2$-Asn$^3$-Cys$^4$-Ala$^5$-Tyr$^6$-His$^7$-Lys$^8$-Gly$^9$-Gln$^{10}$-Ile$^{11}$-Ile$^{12}$-Trp$^{13}$-Cys$^{14}$-Thr$^{15}$-Tyr$^{16}$-His$^{17}$-OH
(S—S bond between Cys$^4$ and Cys$^{14}$) (SEQ ID NO: 2)
m/z[M+H]+ 2088.9

Example 16: Temporary S—S Formation Route by Iodine Oxidation (Folding Concentration: 10 mg/ml)

To a mixed solution of water (0.15 ml), EtOH (0.15 ml), cystine (0.3 mg), and cysteine (0.9 mg) was added the deprotected, temporary S—S formed peptide mixture (3.0 mg) obtained in the above-mentioned Example 15, and aqueous ammonia (3 μl) was added to adjust the pH to 8.5. After 3 hr, the reaction mixture was analyzed by HPLC and it was confirmed that cyclized peptide C was produced at a purity of 55%.

Production Example 7: Completely-Protected Series Peptide D Product

Using Fmoc-Met-OH, Fmoc-Cys(Trt)-OH, Fmoc-Pro-OH, Fmoc-Phe-OH, Fmoc-Thr(tBu)-OH, Fmoc-Asp(OtBu)-OH, Fmoc-His(Trt)-OH, Fmoc-Gln(Trt)-OH, Fmoc-Ala-OH, Fmoc-Arg(Pbf)-OH, Fmoc-Lys(Boc)-OH, Fmoc-Gly-OH, Fmoc-Tyr(tBu)-OH, Fmoc-Leu-OH as starting materials, and di(4-docosoxyphenyl)methylamine (indicated as NHCH$_2$ (Phe (4-OC$_{22}$H$_{45}$))$_2$) as a pseudo-solid-phase protecting group, a completely-protected series peptide D product having the following sequence was synthesized according to a conventional method (see WO 2012/029794; Angew Chem. Int. Ed. 2017. 27, (56), 7803, which are incorporated herein by reference in their entireties). In the present specification, the "completely-protected peptide" is a concept including both a protected N terminal amino group and a non-protected N terminal amino group. Thus, a peptide with non-protected N-terminal is also indicated as a "completely-protected series peptide product". The N-terminal Fmoc group of the following peptide was cleaved with a base according to a conventional method.
Completely-Protected Series Peptide D Product:
H-Met-Cys(Trt)-Met-Pro-Cys(Trt)-Phe-Thr(tBu)-Thr(tBu)-Asp(OtBu)-His(Trt)-Gin(Trt)-Met-Ala-Arg(Pbf)-Lys(Boc)-Cys(Trt)-Asp(OtBu)-Asp(OtBu)-Cys(Trt)-Cys(Trt)-Gly-Gly-Lys(Boc)-Gly-Arg(Pbf)-Gly-Lys(Boc)-Cys(Trt)-Tyr(tBu)-Gly-Pro-Gln(Trt)-Cys (Trt)-Leu-Cys (Trt)-Arg(Pbf)-NHCH$_2$ (Phe (4-OC$_{22}$H$_{45}$))$_2$ Example 17: Temporary S—S Formation Route by Iodine Oxidation (Folding Concentration: 1 mg/ml)

The completely-protected series peptide D product (200 mg) was dissolved in chloroform (3.4 ml) and MeOH (methanol) (0.6 ml), and iodine (8 equivalents, 45.7 mg) was added. After the reaction, the mixture was partitioned twice with an aqueous solution of ascorbic acid (39.6 mg) dissolved in water (3.4 ml), and washed twice with 20% NaCl aqueous solution. The obtained organic layer was concentrated and dried by an evaporator. The solid was deprotected by adding to a mixed solution of TFA (3.9 ml), water (0.1 ml), and p-cresol (24.3 mg). IPE (20 ml) was added and the precipitate was collected by filtration and dried to give a deprotected, temporary S—S formed peptide mixture.

To a mixed solution of water (1 ml), EtOH (1 ml), cystine (0.3 mg), and cysteine (0.3 mg) was added 2.0 mg of the deprotected, temporary S—S formed peptide mixture obtained above, and aqueous ammonia (3 μl) was added to adjust the pH to 9.1. After 1 hr, the reaction mixture was analyzed by HPLC, and it was confirmed that cyclized peptide D was produced at a purity of 49.9%.
Elution Condition
elution time: 3.26 min
instrument used: WATERS ACQUITY UPLC
column: BEH Shield RP18 1.7 μm 2.1×100 mm
temperature: 40° C.
flow rate: 0.30 ml/min
mobile phase: SOLUTION A; 0.05% TFA/H$_2$O SOLUTION B; 0.05%
TFA/MeCN(20)THF(80)
time program (SOLUTION A ratio)
0.00-0.05 min 99%
0.05-13.00 min 99-1%
Cyclized Peptide D:
H-Met$^1$-Cys$^2$-Met$^3$-Pro$^4$-Cys$^5$-Phe$^6$-Thr$^7$-Thr$^8$-Asp$^9$-His$^{10}$-Gln$^{11}$-Met$^{12}$-Ala$^{13}$-Arg$^{14}$-Lys$^{15}$-Cys$^{16}$-Asp$^{17}$-Asp$^{18}$-Cys$^{19}$-Cys$^{20}$-Gly$^{21}$-Gly$^{22}$-Lys$^{23}$-Gly$^{24}$-Arg$^{25}$-Gly$^{26}$-Lys$^{27}$-Cys$^{28}$-Tyr$^{29}$-Gly$^{30}$-Pro$^{31}$-Gln$^{32}$-Cys$^{33}$-Leu$^{34}$-Cys$^{35}$-Arg$^{36}$-NH$_2$
(S—S bond between Cys$^2$ and Cys$^{19}$, Cys$^5$ and Cys$^{28}$, Cys$^{16}$ and Cys$^{33}$, Cys$^{20}$ and Cys$^{35}$) (SEQ ID NO: 3)
m/z[M+4H]4+ 999.6

INDUSTRIAL APPLICABILITY

The present invention provides a production method of a cyclized peptide having a crosslinked structure by one or more intramolecular S—S bonds, which is useful in the field of peptide synthesis.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

---

The invention claimed is:

1. A method for producing a cyclized peptide from a linear peptide, wherein:
the linear peptide comprises two or more SH groups as functional groups,
all SH groups are protected,
an N terminal amino group is optionally protected, and
all of a C-terminal carboxy group and other functional groups on the peptide are protected,
the method comprising:
(1-A) removing protecting groups of all functional groups other than the protected SH groups in the linear peptide;
(1-B) forming a temporary S—S bond to protect all SH groups of the linear peptide;
wherein the peptide obtained from following both (1-A) and (1-B) in any order or both simultaneously is an S-protected peptide,
wherein, in the S-protected peptide:
two or more SH groups are present as the functional groups on the peptide,
all SH groups are protected by formation of a temporary S—S bond, and
all protecting groups of other functional groups on the peptide are removed, and
(2) folding the S-protected peptide under oxidation and reduction conditions to re-form an S—S bond in the S-protected peptide, obtaining the cyclized peptide.

2. The method of claim 1, wherein the forming the temporary S—S bond in (1-B) comprises:
forming a temporary S—S bond with all SH groups within each linear peptide molecule and/or between linear peptide molecules, or
forming a temporary S—S bond with an S-type protecting group.

3. The method of claim 2, wherein the forming the temporary S—S bond in (1-B) comprises temporary S—S formation comprising forming the temporary S—S bond with all SH groups within each linear peptide molecule and/or between linear peptide molecules.

4. The method of claim 3, wherein the forming the temporary S—S bond comprises an iodine treatment or a thallium (III) trifluoroacetate treatment.

5. The method of claim 4, wherein the forming the temporary S—S bond comprises the iodine treatment.

6. The method of claim 3, wherein the S-protected peptide is obtained by subjecting the linear peptide to temporary S—S formation to obtain a mixture of peptides crosslinked or linked by a temporary S—S bond in (1-B), and
the protecting groups of all functional groups other than the SH group protected by temporary S—S bond formation in the mixture of peptides are removed in (1-A).

7. The method of claim 6, wherein the protecting group of the SH group in the linear peptide is a protecting group other than an S-type protecting group.

8. The method of claim 7, wherein the protecting group of the SH group in the linear peptide is a trityl group, an acetamidomethyl group, a benzyl group, a 4-methylbenzyl group, or a 4-methoxybenzyl group.

9. The method of claim 6, wherein the temporary S—S formation comprises an iodine treatment or a thallium (III) trifluoroacetate treatment.

10. The method of claim 9, wherein the temporary S—S formation comprises an iodine treatment.

11. The method of claim 3, wherein the S-protected peptide is obtained by removing the protecting groups of all functional groups other than the SH group of the linear peptide in (1-A) to form a deprotected peptide, and then or simultaneously subjecting the deprotected peptide to temporary S—S formation in (1-B) to obtain a temporary S—S formed peptide mixture.

12. The method of claim 11, wherein the protecting group of the SH group of the linear peptide is a protecting group other than an S-type protecting group.

13. The method of claim 12, wherein the protecting group of the SH group of the linear peptide is an acetamidomethyl group, a t-butyl group, a trityl group, a benzyl group, a 4-methylbenzyl group, or a 4-methoxybenzyl group.

14. The method of claim 11, wherein the temporary S—S formation comprises an iodine treatment, a DMSO/TFA treatment, or a thallium (III) trifluoroacetate treatment.

15. The method of claim 14, wherein the temporary S—S formation comprises an iodine treatment.

16. The method of claim 3, wherein the S-protected peptide is obtained by
a)
  1) After removing the protecting groups of all functional groups other than the SH group in (1-A),
  2) Removing the protecting group of the SH group, and further
  3) carrying out temporary S—S formation in (1-B) to obtain a temporary S—S formed peptide mixture, or
b)
  1) After removing the protecting group of the SH group of the linear peptide,
  2) Carrying out temporary S—S formation in (1-B) to obtain a temporary S—S formed peptide mixture, and further
  3) Removing the protecting groups of all functional groups other than the SH group protected by temporary S—S bond formation in the temporary S—S formed peptide mixture in (1-A).

17. The method of claim 16, wherein the protecting group of the SH group is a protecting group other than an S-type protecting group.

18. The method of claim 17, wherein the protecting group of the SH group is a phenylacetamidomethyl group, a 4-methoxybenzyl group, or a mono methoxytrityl group.

19. The method of claim 18, wherein the protecting group of the SH group is removed by a treatment with an aqueous solution in the presence of penicillin amidohydrolase, a treatment with DDQ, or a treatment with a weak acid.

20. The method of claim 16, wherein the temporary S—S formation comprises an iodine treatment, an Npys-OMe treatment, or a thallium (III) trifluoroacetate treatment.

21. The method of claim 20, wherein the temporary S—S formation comprises an iodine treatment.

22. The method of claim 2, wherein the forming a temporary S—S bond in (1-B) comprises forming a temporary S—S bond with an S-type protecting group.

23. The method of claim 22, wherein the protection of all SH groups by forming a temporary S—S bond in (1-B) is performed by re-protecting the SH group with an S-type protecting group instead of a protecting group other than an S-type protecting group.

24. The method of claim 22, wherein the S-type protecting group is a 3-nitro-2-pyridinesulfenyl group, a t-butylmercapto group, or an ethylmercapto group.

25. The method of claim 22, wherein the S-protected peptide is obtained by
re-protecting protecting groups of SH groups of a linear peptide having two or more SH groups as functional groups on the peptide, in which an N terminal amino group is optionally protected, and all of a C-terminal carboxy group and other functional groups on the peptide are protected, with an S-type protecting group, or
protecting same with an S-type protecting group in advance to obtain a peptide in which all SH groups are protected by formation of a temporary S—S bond with the S-type protecting group in (1-B), and
removing the protecting groups of all functional groups other than the SH group protected by the temporary S—S bond in the peptide in (1-A).

26. The method of claim 1, wherein the deprotection is performed in the absence of a reducing agent.

27. The method of claim 1, wherein the folding under the oxidation and reduction conditions in (2) is performed in an aqueous solution with pH 6 or higher.

28. The method of claim 1, wherein the folding under the oxidation and reduction conditions in (2) is performed in the co-presence of an oxidant and a reducing agent.

29. The method of claim 1, wherein the number of SH groups as the functional group on the peptide of the S-protected peptide is 2.

30. The method of claim 1, wherein the number of SH groups as the functional groups on the peptide of the S-protected peptide is not less than 4.

31. The method of claim 1, wherein the number of SH groups as the functional groups on the peptide of the S-protected peptide is an even number.

* * * * *

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: cyclic peptide A
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 17
<212> TYPE: PRT
<213> ORGANISM: Artificial Sequence
<220> FEATURE:
<223> OTHER INFORMATION: cyclic peptide C
<220> FEATURE:
<221> NAME/KEY: DISULFID
<222> LOCATION: (4)..(14)

<400> SEQUENCE: 2

Arg Gly Asn Cys Ala Tyr His Lys Gly Gln Ile Ile Trp Cys Thr Tyr
1               5                   10                  15

His
```

```
<210> SEQ ID NO 3
<211> LENGTH: 36
<212> TYPE: PRT
<213> ORGANISM: Artificial Sequence
<220> FEATURE:
<223> OTHER INFORMATION: cyclic peptide D
<220> FEATURE:
<221> NAME/KEY: DISULFID
<222> LOCATION: (2)..(19)
<220> FEATURE:
<221> NAME/KEY: DISULFID
<222> LOCATION: (5)..(28)
<220> FEATURE:
<221> NAME/KEY: DISULFID
<222> LOCATION: (16)..(33)
<220> FEATURE:
<221> NAME/KEY: DISULFID
<222> LOCATION: (20)..(35)
<220> FEATURE:
<221> NAME/KEY: MOD_RES
<222> LOCATION: (36)..(36)
<223> OTHER INFORMATION: AMIDATION

<400> SEQUENCE: 3

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35
```